United States Patent
Vial et al.

(10) Patent No.: US 7,256,170 B2
(45) Date of Patent: Aug. 14, 2007

(54) SPIRO COMPOUNDS AS PERFUMING INGREDIENTS

(75) Inventors: Christian Vial, Lathoy (FR); Robert Moretti, Laconnex (CH); Alain Charpilloz, Geneva (CH); Peter Fankhauser, Meyrin (CH); Piero Fantini, Veyrier (CH)

(73) Assignee: Firmenich SA, Geneva (CH)

( * ) Notice: Subject to any disclaimer, the term of this patent is extended or adjusted under 35 U.S.C. 154(b) by 552 days.

(21) Appl. No.: 10/680,138

(22) Filed: Oct. 8, 2003

(65) Prior Publication Data
US 2004/0072721 A1  Apr. 15, 2004

(30) Foreign Application Priority Data
Oct. 14, 2002  (WO) .............. PCT/IB02/04217

(51) Int. Cl.
*A61Q 19/00* (2006.01)
*A61Q 19/10* (2006.01)
*A61Q 13/00* (2006.01)
*C07D 493/00* (2006.01)
*C07D 311/96* (2006.01)

(52) U.S. Cl. .............. 512/25; 510/130; 512/1; 512/9; 512/14; 512/15; 512/16; 549/330; 549/331

(58) Field of Classification Search .......... 512/9, 512/14, 15, 16, 25, 1; 510/130; 549/330, 549/331
See application file for complete search history.

(56) References Cited

U.S. PATENT DOCUMENTS

| 4,052,457 | A | * | 10/1977 | Nagakura et al. | ........ 568/349 |
|---|---|---|---|---|---|
| 4,336,197 | A | * | 6/1982 | Fankhauser | ............ 549/331 |
| 4,448,712 | A | * | 5/1984 | van der Weerdt et al. | ...... 512/9 |
| 4,537,702 | A | * | 8/1985 | van der Weerdt et al. | .. 426/536 |
| 4,622,172 | A | * | 11/1986 | Schreiber et al. | ......... 424/47 |
| 4,639,330 | A | * | 1/1987 | Sprecker et al. | .......... 512/9 |
| 4,668,432 | A | * | 5/1987 | Sprecker et al. | .......... 512/9 |

OTHER PUBLICATIONS

English Abstract, XP-002266544, N. B. Novikova, et al "Synthesis and structure of some dimethyl-substituted spiro[5.5]undecenes and undeca-1, 8dienes", (1984).

English Abstract, XP-002266545, N. B. Novikova, et al, "Synthesis, stereochemistry, and equilibrium ratios isomers of 1,6-1, 7-, and1, 8-dimethylspiro[4.5] decanes" (1986).

English Abstract, JP 01258634, "Spiro (4,5) decene derivative, production thereof and perfume composition containing the same derivative" (1989).

Nakamura et al., "α-metylenation/diels-alder tandem reaction promoted by ammonium salts generated in situ from secondary-tertiary diamines and alkoxymethyl chlorides", Chem. Commun., pp. 1648-1649 (2002).

* cited by examiner

*Primary Examiner*—Jill Warden
*Assistant Examiner*—Lore Ramillano
(74) *Attorney, Agent, or Firm*—Winston & Strawn LLP

(57) ABSTRACT

The present invention relates to the perfumery industry. It concerns more particularly an alcohol, ester, ether or ketone derivative having a spiro-type skeleton, the latter being substituted by short alkyl groups. The invention also relates to the use of the invention compounds as perfuming ingredients, able to impart a woody and/or aromatic, as well as to the perfumed articles or perfuming compositions comprising as active ingredient a compound of formula (I).

22 Claims, No Drawings

SPIRO COMPOUNDS AS PERFUMING INGREDIENTS

BACKGROUND ART

Alcohol, ester, ether or ketone derivatives having a spiro-type skeleton are a quite well known class of chemicals. However, and surprisingly, despite the large number of structures reported in the prior art, only a few compounds of formula (I), hereinbelow described, are known.

For instance, Novikova et al. in their Naftekhimiya, 1984, 24, 475 paper disclose, as chemical intermediates, a mixture of the ketones 2,8-dimethyl spiro[5,5]undec-8-en-1-one and 2,9-dimethyl spiro[5,5]undec-8-en-1-one, as well as a mixture of the tertiary alcohols 1,9-dimethyl spiro[5,5]undec-8-en-1-ol and 1,8-dimethyl spiro[5,5]undec-8-en-1-ol. The same authors in their Naftekhimiya, 1986, 26, 3 paper disclose, still as chemical intermediates, a mixture of the tertiary alcohols 1,7-dimethyl spiro[4,5]dec-7-en-1-ol and 1,8-dimethyl spiro[4,5]dec-7-en-1-ol.

Furthermore, Nakamura et al. in Chem.Commun, 2002, 1648 disclose, as chemical compounds, the two spiro-ketones 8,9-dimethyl spiro[5,5]undec-8-en-1-one and 7,8-dimethyl spiro[4,5]dec-7-en-1-one.

However, there is no mention or suggestion, in any of said documents mentioned hereinabove, of the specific organoleptic properties of the invention's compounds, or of any potential usefulness of said compounds as perfuming ingredients.

Amongst the compounds having a structure similar to that of the compounds of the present invention, only few are known in the prior art to have an odor which may be of interest for the perfumery industry. In U.S. Pat. No. 4,668,432 there are reported some alkyl substituted oxo-spiro[4,5]dec-7-ene derivatives which possess odors dominated by minty or animal top-notes. Similarly, U.S. Pat. No. 4,622,172 discloses 9-methyl-11-isopropyl-spiro[5,5]undec-8-ene which imparts to compositions a fresh minty and spicy aroma. All the compounds disclosed in U.S. Pat. Nos. 4,668,432 and 4,622,172 have a structure and an odor which differ from those of the compounds of the present invention.

SUMMARY OF THE INVENTION

The present invention relates to the perfumery industry. It concerns more particularly a perfuming composition comprising at least a specific alcohol, ester, ether or ketone derivative having a spiro-type skeleton. The invention concerns also the compounds themselves as well as their use as perfuming ingredients. The invention also relates to the perfumed articles comprising, as active ingredient, an invention compound.

DETAILED DESCRIPTION OF THE PREFERRED EMBODIMENTS

We have now surprisingly been able to establish that a compound of formula

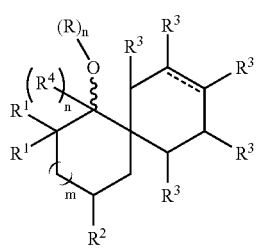

(I)

wherein the index m represents 0 or 1;
R represents a hydrogen atom, or a methyl or acetyl group;
$R^1$, $R^2$ and $R^4$ represent a hydrogen atom or a methyl group;
$R^3$ represents a hydrogen atom, or a methyl or ethyl group; two, three or four of all the $R^1$, $R^2$, $R^3$ and $R^4$ representing simultaneously a group containing at least a carbon atom; and
the wavy and dotted lines represent a double bond, in which case n represents 0; or
the wavy line represents a single bond, in which case the index n represents 1; and the dotted line represents a single or double bond;
possesses useful perfuming properties, of the woody and/or aromatic type, which render them very useful for the perfumery industry.

It is understood that, in a compound of formula (I), each of said $R^1$ or $R^3$ may be identical or different to other $R^1$ or $R^3$, respectively. Moreover, the compound of formula (I) may be in the form of any one of its optical isomers or of its diastereomers or yet a mixture of any one of said isomers.

Moreover, the compositions consisting of at least two compounds of formula (I), from now on referred to also as a mixture of compounds of formula (I), and preferably of regio isomers, are also useful perfuming ingredients and therefore are part of the present invention. By "regio isomers" it is meant here the compounds which differ by the position in which one or more $R^3$, not representing a hydrogen atom, are bonded to the spiro-skeleton. As non-limiting example of "regio isomers" one can cite 6,8,10-trimethyl-spiro[4.5]dec-7-en-1-one and its regio isomer 7,9,10-trimethyl-spiro[4.5]dec-7-en-1-one.

Preferred mixtures of compounds of formula (I) are those containing essentially, e.g. as major constituents, two regio isomers of formula (I).

Another embodiment of the invention is illustrated by the compounds of formula

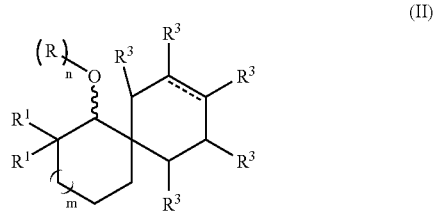

(II)

wherein n, m, R, $R^1$, $R^3$, the wavy line and the dotted line have the same meaning as indicated in formula (I).

Preferably, the compounds of formula (II) are those wherein the indexes m and n and the dotted and wavy lines have the same meaning as in formula (I);
R represents a hydrogen atom or an acetyl group;
$R^1$ and $R^3$ represent a hydrogen atom or a methyl group; two, three or four of all the $R^1$ and $R^3$ representing simultaneously a methyl group and one, two or three of all the $R^3$, preferably non adjacent, representing simultaneously a methyl group.

Another preferred embodiment of the invention's compound is a compound of formula (II) wherein m, n and the dotted and wavy lines have the same meaning as in formula (I); and
R represents a hydrogen atom or an acetyl group;
one $R^1$ is a hydrogen atom and the other $R^1$ represents a hydrogen atom or a methyl group;
$R^3$ represents a hydrogen atom or a methyl or ethyl group; two, three or four of all the $R^1$ and $R^3$ being a group containing at least a carbon atom and one, two or three of all the $R^3$, preferably non adjacent, representing a methyl or ethyl group.

It is understood that, as for the compound of formula (I), each of said $R^1$ or $R^3$ may be identical or different to the other $R^1$ or $R^3$, respectively.

A particularly useful embodiment of the invention is represented by the alcohol or ester of the formula (III)

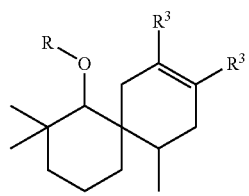

(III)

wherein R represents a hydrogen atom or an acetyl group; and
the $R^3$ are identical and represent a hydrogen atom or the $R^3$ are different and represent a hydrogen atom or a methyl group.

Alternatively, another useful embodiment of the invention is represented by the ketone of formula (IV)

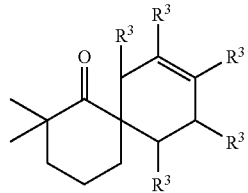

(IV)

wherein two, preferably non adjacent, $R^3$ represent a methyl group and the other $R^3$ represent a hydrogen atom.

Yet alternatively, one may cite also the compounds of formula

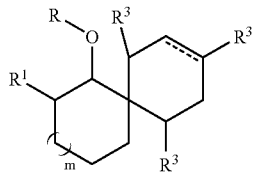

(V)

wherein R represents a hydrogen atom or an acetyl group;
$R^1$ represents a hydrogen atom or a methyl group; and
$R^3$ represents a hydrogen atom or a methyl or ethyl group and at least two $R^3$ represent a methyl group; and
m is 1 and the dotted line represents a single bond, or
m is 0 and the dotted line represents a double bond.

The compounds of formula (II), (III), (IV) and (V), like those of formula (I), may be in the form of any one of their optical isomers or diastereoisomers or of a mixture thereof.

The invention's spiro compounds are obtainable by a process involving a thermal, or a Lewis acid, catalyzed Diels-Alder reaction between an enone of formula (VI) or, alternatively, its equivalent Mannich base of formula (VI)

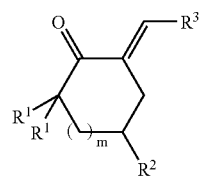

(VI)

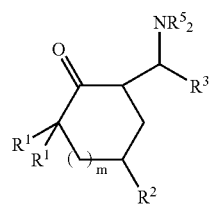

(VII)

wherein the index m and $R^1$, $R^2$ and $R^3$ are as defined in formula (1) and the $R^5$ represent, if taken independently, a methyl, ethyl, propyl or isopropyl group, or, if taken together with the nitrogen atom to which they are bound, a $C_5$-$C_7$ saturated heterocycle such as morpholine, piperidine or pyrrolidine;
and a diene of formula (VIII)

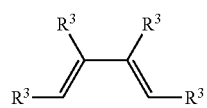

(VIII)

wherein $R^3$ are as defined in formula (I), to provide a spiro-ketone (IX)

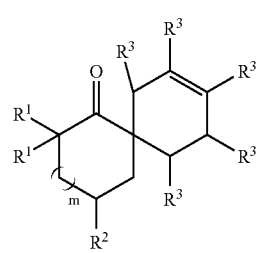

(IX)

wherein the index m and $R^1$, $R^2$ and $R^3$ are as defined in formula (I).

Typical catalysts that can be used in the acid catalyzed Diels-Alder are $AlCl_3$, $FeCl_3$ or $BF_3.Et_2O$.

The reaction temperature of the Diels-Alder depends on the type of catalyst. In the case of a thermal reaction, the temperature range is comprised between −100° C. and 240° C., preferably between 140° C. and 200° C. In the case where a Lewis acid is used, the temperature range is comprised between −40° C. and 30° C., preferably between −30° C. and 20° C.

The Diels-Alder reaction may be performed in the absence or in the presence of a solvent. When a solvent is used then any current solvent in Diels-Alder reactions can be used for the purposes of the invention, provided that it is compatible with the starting and final products. Non-limiting examples include aromatic solvents such as toluene or xylene, or alternatively, for acid catalyzed reactions there can be used solvents such as $CH_2Cl_2$, toluene or $CH_3CN$.

It will be also understood that whenever the diene (VIII) is not a symmetric compound, then the Diels-Alder reaction may lead to the formation of a mixture of spiro-ketones of formula (IX), more precisely to a mixture of regio isomers. Additionally, as the spiro-ketone (IX) possesses several chiral centers, said ketone may also be obtained in the form of a mixture of optically active isomers or of diastereomers or yet a mixture of any one of said isomers.

As well known to a person skilled in the art, the relative ratio of all the possible isomers obtained may depend on the nature of the starting compounds (VIII) and (VI) or (VII), as well as on the experimental conditions and possibly on the nature of the catalyst used.

The spiro-ketone (IX) thus obtained may subsequently be reduced, e.g. using an alkalin metal, an hydride such as $LiAlH_4$ or an alkylating agent such as MeLi, to the corresponding spiro-alcohol of formula (X)

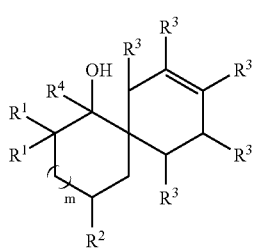

(X)

wherein the index m and the symbols $R^1$, $R^2$, $R^3$ and $R^4$ have the meaning indicated in formula (I).

If desired, using conventional methods well known to a person skilled in the art, the spiro-alcohol (X) may subsequently be converted into an ester or an ether. Also, if desired, the carbon carbon double bond of the spiro-ketone (IX) or the spiro-alcohol (X), or its derivatives, can be reduced, e.g. by hydrogenation.

A specific example of the overall process is given in scheme (1):

Scheme (1):
Example of the synthetic pathway to compounds of formula (I)

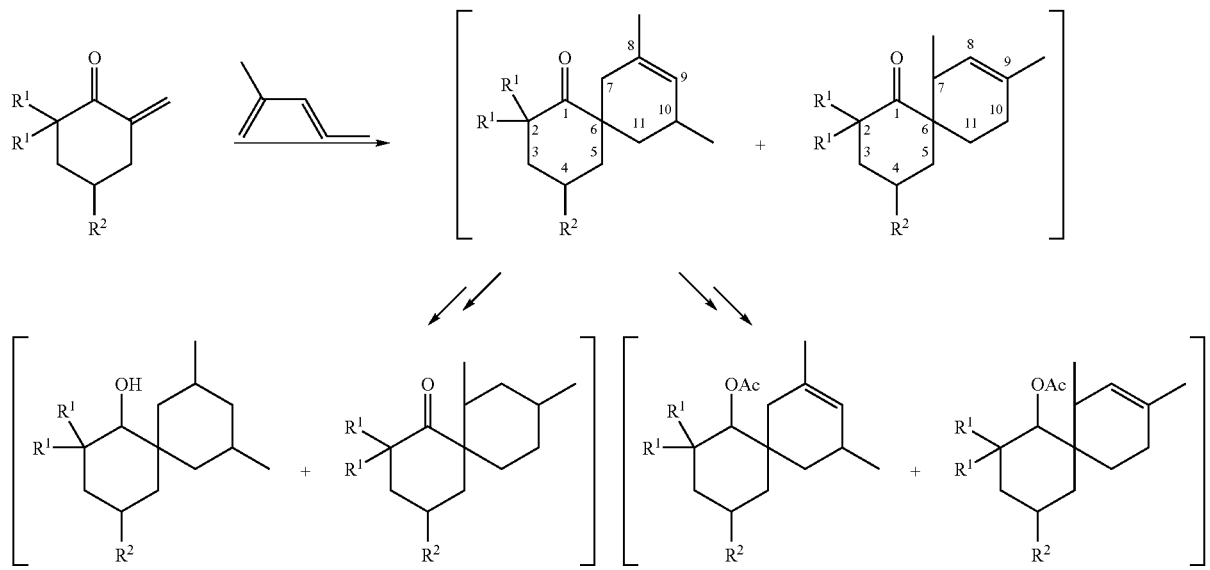

As previously mentioned, the compounds of formula (I) have odor properties which render them very useful for the perfumery industry. More precisely, the compounds of formula (I) display woody and/or aromatic fragrances, and are devoid of the minty or animal typical character of the prior art spiro-derivatives mentioned above. New compounds having such odor properties are highly desirable in the perfumery industry.

Examples of invention's compounds are various, as will become apparent below and in the examples.

An example is 2,2,9,11-tetramethylspiro[5.5]undec-8-en-1-yl acetate. Said compound has a very powerful woody odor with an excellent amber/ambergris connotation. The amber/ambergris notes, which are quite tenacious and strong, are well perceivable as top note as well as bottom notes. The overall odor is reminiscent of the Amberwood® (origin BASF AG) or 8,13:13,20-diepoxy-15,16-dinorlabdane (origin: Firmenich SA) odor. In addition to its excellent odor, 2,2,9,11-tetramethylspiro[5.5]undec-8-en-1-yl acetate seems to also have the advantage of not inducing anosmia, unlike many prior art compounds of the same olfactive family.

Another example of a compound according to the invention and belonging to the woody olfactive family is 2,2,11-trimethylspiro[5.5]undec-8-en-1-ol, which has an excellent woody odor with camphor and earthy notes. Its overall odor is characterized by a very appreciated and substantive musky and woody-rooty undernote of the patchoulicvetyver type, reminiscent of Tonalide® (origin: PFW, Holland), lasting more than a week on a smelling strip. Thanks to its characteristic undernote, 2,2,11-trimethylspiro[5.5]

undec-8-en-1-ol has the remarkable ability to confer richness, volume and persistence to a perfuming composition.

The saturated analogue of the previous compound, i.e. 2,2,11-trimethylspiro[5.5]undecan-1-ol, has an odor which is very similar to, but drier, than that of 2,2,11-trimethylspiro[5.5]undec-8-en-1-ol.

A mixture of 2,2,7,9-tetramethylspiro[5.5]undec-8-en-1-one and its regio isomer 2,2,8,10-tetramethylspiro[5.5]undec-8-en-1-one possesses a quite complex odor profile but clearly belonging to the aromatic family. The fragrance of said mixture has aromatic, spicy, cardamom and terpenic notes, as well as camphor-woody under notes and a sulfury connotation, so that the whole scent is reminiscent of the eucalyptus and clary-sage essential oils. Said mixture is well appreciated by perfumers for its very useful aromatic note which is recalling that of the noble laurel essential oil, an oil which can be used only in very limited amounts. Moreover, it has been found that the performance of said mixture in functional perfumery, e.g. softeners or detergents, is remarkable when compared to other products of the same olfactive family.

The lower analogues of the above-mentioned mixtures, e.g. having only three or two methyl substituents, have odors which tend to have different aromatic notes, as well as to be more camphoraceous and more volatile of the previous one. For instance a mixture of 2,2,10-trimethylspiro[5.5]undec-8-en-1-one and 2,2,7-trimethylspiro [5.5]undec-8-en-1-one has a pleasant and natural fragrance which is more camphor, woody, juniper and lavender than its tetramethyl analogue mentioned above, while 2,2-dimethylspiro[5.5]undec-8-en-1-one possesses an odor which is more terpeny, camphor, earthy and slightly tagetes than its tetramethyl analogue mentioned above.

Another example of a mixture of compounds of formula (I) is the mixture of regio-isomers 6,8-dimethyl-spiro[4.5] dec-7-en-1-yl acetate and 7,9-dimethyl-spiro [4.5]dec-7-en-1-yl acetate which possess a tenacious woody, cedar and amber odor with a sawdust connotation.

As example of a compound of formula (I) in the form of a specific diastereomer, one can cite (1RS,6RS,11RS)-2,2,9,11-tetramethylspiro[5.5]undec-8-en-1-yl acetate and (1RS,6SR,11SR)-2,2,9,11-tetramethylspiro[5.5]undec-8-en-1-yl acetate which possess a good woody, amber odor, the latter compound being preferred by the perfumers for its more powerful odor. Furthermore one may also cite (1RS, 6RS,11RS)-2,2,11-trimethylspiro[5.5]undec-8-en-1-ol which possesses an odor more woody and slightly less patchouli than the 2,2,11-trimethylspiro[5.5]undec-8-en-1-ol, mentioned above.

Thus, a particularly interesting embodiment of the invention, for the perfumers, is represented by 2,2,9,11-tetramethylspiro[5.5]undec-8-en-1-yl acetate or 2,2,11-trimethylspiro[5.5]undec-8-en-1-ol or yet a mixture of 2,2,7,9-tetramethylspiro[5.5]undec-8-en-1-one and 2,2,8,10-tetramethylspiro[5.5]undec-8-en-1-one. Similarly, an interesting embodiment of the invention is represented by 2,2,11-trimethylspiro[5.5]undecan-1-ol, 2,2-dimethylspiro[5.5]undec-8-en-1-one, (1RS,6SR,11SR)-2,2,9,11-tetramethylspiro[5.5]undec-8-en-1-yl acetate, (1RS,6RS,11RS)-2,2,11-trimethylspiro[5.5]undec-8-en-1-ol, (1RS,6RS,11RS)-2,2,9,11-tetramethylspiro[5.5]undec-8-en-1-yl acetate or a mixture of 2,2,10-trimethylspiro[5.5]undec-8-en-1-one and 2,2,7-trimethylspiro[5.5]undec-8-en-1-one or a mixture of 6,8-dimethyl-spiro[4.5]dec-7-en-1-yl acetate and 7,9-dimethyl-spiro[4.5]dec-7-en-1-yl acetate. Another interesting embodiment of the invention is represented by the compounds 2,6,8-trimethylspiro[4.5]dec-7-en-1-ol or 7-ethyl-11-methylspiro[5.5]undecan-1-ol, which are described further below.

As mentioned above, the invention concerns also the use of a compound of formula (I), or of a mixture of compounds of formula (I), as perfuming ingredients. In other words it concerns a method to confer, enhance, improve or modify the odor properties of a perfuming composition or of a perfumed article, which method comprises adding to said composition or article an effective amount of at least a compound of formula (I). By "use of at least a compound of formula (I)" it has to be understood here the use of one or more compounds (I) in any of their forms which can be advantageously employed in perfumery as active ingredients.

Said forms are also an object of the present invention.

In an embodiment of the invention, one of said forms, which can be advantageously employed as perfuming ingredient, is a composition of matter consisting of at least a compound of formula (I) and at least one perfumery carrier. By "perfumery carrier" we mean here one or more materials which are able to be admixed with at least an invention's compound without significantly altering its organoleptic properties, e.g. materials which are practically neutral from a perfumery point of view. Said carrier may be a liquid or a solid.

As liquid carrier one may cite, as non-limiting examples, an emulsifying system, i.e. a solvent and a surfactant system, or a solvent commonly used in perfumery. As examples of solvents commonly used in perfumery, generally speaking, one can cite compounds such as dipropyleneglycol, diethyl phthalate, isopropyl myristate, benzyl benzoate, 2-(2-ethoxyethoxy)-1-ethanol or ethyl citrate, which are the most commonly used. As solid carrier one may cite, as non-limiting examples, an absorbing gum or polymers, or yet an encapsulating material, said materials are well known to a person skilled in the art.

In another embodiment of the invention, a suitable form of the invention's compound is a composition of matter comprising at least one compound of formula (I), or a composition of matter mentioned above, and a perfume base. In other words the compound (I) is in the form of a perfuming composition comprising at least one invention's compound as perfuming ingredient. It is understood that the perfuming ingredients are present in a perfuming effective amount.

Generally speaking, by "perfume base" we mean here a composition comprising at least one perfuming co-ingredient and possibly one or more solvents or adjuvants commonly used in the perfume industry.

Said perfuming co-ingredients are not of the formula (I). Moreover, by "perfuming co-ingredient" it is meant here a compound, which is of current use in perfumery industry, i.e. a compound which is used as ingredient in perfuming preparation or composition in order to impart an hedonic effect. In other words such a co-ingredient, to be considered as being a perfuming one, must be recognized by a person skilled in the art as being able to impart or modify in a positive or pleasant way the odor of a composition, and not just as having an odor. It is also understood here that, unless otherwise indicated or described, any mixture resulting directly (e.g. without purification) from a chemical synthesis in which the compound of the invention would be involved as a starting intermediate or as an end-product could not be considered as a perfuming composition according to the invention.

The nature and type of the perfuming co-ingredients present in the base do not warrant a more detailed description here, which in any case would not be exhaustive, the skilled person being able to select them on the basis of its general knowledge, and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

Similarly, a detailed description of the nature and type of solvents commonly used in perfuming bases cannot be exhaustive. A skilled person in the art is able to select them on the basis of the nature of the product to be perfumed. However, as non-limiting examples of solvents commonly used in perfumery bases, one can cite, in addition to the solvents mentioned above, also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

The perfuming compositions according to the invention may be a simple mixture of the various co-ingredients and solvents, or be also in the form of a bi-phasic system such as an emulsion or microemulsion. Alternatively, said perfuming compositions can be incorporated into a solid perfumery carrier, as defined above.

It is useful to mention here that the possibility to have, in the compositions of matter mentioned above, more than one compound of formula (I) is important as it enables the perfumer to prepare accords, perfumes, possessing the odor tonality of various compounds of the invention, creating thus new tools for their work.

Furthermore, as mentioned above, a compound of formula (I) is a useful perfuming ingredient and therefore can be advantageously used in all the fields of modern perfumery to positively impart or modify the odor of a consumer product into which said compound (I), in any of its forms, is added. Consequently, a perfumed article comprising:

i) at least one compound of formula (I), or a composition of matter mentioned above; and
ii) a consumer product base, is also an object of the present invention.

For the sake of clarity, it has to be mentioned that, by "consumer product base" we mean here a consumer product, i.e. a consumable product such as a detergent or a perfume. In other words, a perfumed article according to the invention essentially comprises the functional formulation, as well as optionally additional benefit agents, corresponding to a desired consumer product, e.g. a detergent, and an olfactive effective amount of at least an invention's compound, in any of its forms.

The nature and type of the constituents of the consumer product do not warrant a more detailed description here, which in any case would not be exhaustive, the skilled person being able to select them on the basis of its general knowledge and according to the nature and the desired effect of said product.

Examples of suitable unperfumed consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compounds, so that it may be necessary to protect the latter from premature decomposition, for example by encapsulation.

The proportions in which the compounds according to the invention can be incorporated into the various aforementioned articles or compositions vary within a wide range of values. The range of concentrations depends on the nature of invention compound used, on the nature of the product to be perfumed and on the olfactory effect sought, as well as on the nature of the co-ingredients in a given composition when the compounds of the invention are used in admixture with perfuming co-ingredients, solvents or additives commonly used in the art.

For instance, concentrations from 0.01% to 10.0%, by weight of these compounds, can be typically used. Preferably, for the powerfully odorant invention's compounds or mixtures of compounds, typical concentrations are from 0.1% to 3%, by weight of these compounds, while for the less powerful ones it is preferred to use concentrations ranging from 0.5% to 5%, by weight. All the above percentages are expressed with respect to the weight of the perfuming composition in which the invention compounds are incorporated.

Lower concentrations than these can be used when these compounds are directly applied for perfuming some of the consumer products mentioned above.

The invention will now be described in further detail by way of the following examples, wherein the abbreviations have the usual meaning in the art, the temperatures are indicated in degrees centigrade (° C.); the NMR spectral data were recorded with a 360 MHz machine in CDCl$_3$, the chemical displacement δ are indicated in ppm with respect to the TMS as standard, the coupling constant J are expressed in Hz and all the abbreviations have the usual meaning in the art.

EXAMPLE 1

Synthesis of some Compounds According to the Invention or Useful as Intermediate a) A Mixture of 7,9-dimethyl-spiro[5.5]undec-8-en-1-one and 8,10-dimethyl-spiro[5.5]undec-8-en-1-one A 5 l stainless steel autoclave was charged with cyclohexanone (1529 g; 15.6 mol), 2-methyl-1,3-pentadiene (984 g; 12 mol), BHT (2.4 g) and 37% aqueous formaldehyde (488 g; 180.56 g of pure formaldehyde; 6.02 mol). The mixture was heated to 200° C. under stirring for 7 hours. After cooling to room temperature, the aqueous phase was discarded, and the organic phase washed with brine, affording a crude product. Distillation through a 70 cm Sulzer column afforded 447.5 g of pure product as a mixture of 4 isomers in the ratio 4/7/55/34 (B.p.=82° C.; 1mbar). Yield: 38.7%.

Organoleptic properties: woody odor with floral and herbaceous connotation

MS (major isomer): 39 (15); 41 (24); 55 (17); 67 (49); 77 (20); 79 (20); 82 (100); 91 (28); 93 (23); 105 (13); 107 (18); 111 (10); 119 (6); 121 (11); 135 (9); 149 (16); 159 (5); 163 (8); 174 (2); 177 (8); 192 (M+, 19).

MS (second major isomer): 39 (30); 41 (44); 55 (30); 67 (64); 77 (37); 79 (37); 82 (100); 91 (53); 93 (41.); 105 (28); 107(44); 109 (12); 119 (19); 121 (24); 135 (42); 149 (32); 150 (6); 159 (15); 163 (19); 174 (6); 177 (20); 192 (M+, 34).

$^1$H-NMR: 5.27 (isomer C) and 5.18 (isomer D) (br s, 1H); 2.60-1.43 (m, 11H); 1.64 (s, 3H); 1.37-1.20 (m, 2H); 0.83 (isomer D) (d, J=7 Hz, 3H); 0.78 (isomer C) (d, J=7 Hz, 3H).

b) (5RS,6SR,10SR)-10-Ethyl-6,8-dimethyl spiro [4.5]dec-7-en-1-one

Propylidene cyclopentanone (E/Z: 9/1) (248 g; 2 mol) and toluene (200 ml) were charged in a multi-necked 2 l round bottom flask and the solution cooled to 0° C. BF$_3$ etherate (20 ml) was added dropwise over 25 minutes, while maintaining the reaction mixture at 0° C. Stirring at 0° C. was continued for one hour, after which a solution of 2-methyl-1,3-pentadiene (410 g; 5 mol) in toluene (200 ml) was added dropwise over 3 hours. The reaction mixture was then stirred at 0° C. for 3 hours and then poured onto ice. The aqueous phase was discarded and the organic phase washed with water, Na$_2$CO$_3$ aqueous solution, and brine. Drying on MgSO$_4$, filtration and removal of the solvent afforded the crude cycloadduct. A rapid distillation followed by a second distillation through a 10 cm Vigreux column gave a cycloadducts as a mixture of isomers (79/5/16) and in a yield of 81.4%. Distillation of the latter through a 35 cm Fischer Spaltrohr® column allowed to isolate the main isomers, being the title compound.

Organoleptic properties: sage odor with a fruity and damascone connotation

MS: 27 (51); 29 (51); 39 (54); 41 (80); 43 (31); 51 (14); 53 (29); 55 (44); 65 (35); 67 (77); 69 (11); 77 (47); 79 (43); 82 (100); 91 (68); 93 (40); 96 (55); 105 (38); 107 (55); 111 (14); 119 (17); 121 (35); 125 (34); 133 (19); 135 (34); 149 (38); 159 (52); 163 (33); 173 (12); 177 (74); 188 (25); 191 (11); 206 (16).

$^1$H-NMR: 5.27 (br s, 1H); 2.38-2.27 (m, 1H); 2.20-2.00 (m, 3H); 1.92-1.70 (m, 5H); 1.65 (s, 3H), 1.46 (dd, J=17 Hz, 12 Hz, 1H); 1.32-1.21 (m, 1H); 1.06-0.75 (m, 1H); 0.91 (t, J=8 Hz, 3H); 0.87 (d, J=8 Hz, 3H).

$^{13}$C-NMR: 222.7 (s); 132.2 (s); 124.9 (d); 55.1 (s); 39.6 (t); 35.9 (d); 34.2 (d); 33.4 (t); 29.9 (t), 23.9 (t); 23.3 (q); 18.1 (t); 17.3 (q); 12.2 (q).

c) R-6-Ethyl-T-10-methyl-spiro[4.5]decan-1-one i) 6-Ethyl-10-methyl-spiro[4.5]dec-8-en-1-one A solution of propylidene cyclopentanone (obtained according to N. Katsin, R. Ikan, Synth. Comm. 1977, 7(3), 185) (248 g; 2 mol) in toluene (200 g) was cooled to 0° C. boron trifluoride etherate (20 ml) were added at 0° C. over 10 minutes. 1,3-pentadiene (E/Z mixture; 348 g; 5 mol), dissolved in toluene (200 g) was then added dropwise over 3 hours at 0° C. Stirring was continued at 0° C. for 3 hours. Usual work-up (se above) afforded the crude product. Flash distillation followed by a second purification through a 15 cm Vigreux column gave 198.4 g of a cycloadducts as a mixture of two isomers (Yield: 51.7%). Further distillation through a 35 cm Fischer Spaltrohr® column afforded the pure isomers R-6-Ethyl-T-10-methyl-spiro[4.5]dec-8-en-1-one and R-6-Ethyl-C-10-methyl-spiro[4.5]dec-8-en-1-one.

R-6-Ethyl-T-10-methyl-spiro[4.5]dec-8-en-1-one (major isomer)

Organoleptic properties: aromatic and thujonic odor

MS: 192 (M+, 45); 177 (6); 174 (7); 163 (100); 149 (13); 145 (36); 135 (29); 125 (50); 121 (31); 119 (13); 111 (43); 107 (47); 105 (27); 93 (78); 91 (76); 82 (27); 79 (66); 77 (53); 67 (56%); 65 (27); 59 (10); 55 (41); 53 (32); 41 (60); 39 (46); 29 (26); 27 (33);

$^1$H-NMR: 5.62 (m, 1H); 5.55 (m, 1H); 2.38-2.02 (m, 4H); 1.94-1.75 (m, 4H); 1.60-1.48 (m, 1H); 1.32-1.20 (m, 1H); 1.12-0.87 (m, 2H); 0.91 (d and t, J=8 Hz, 6H).

$^{13}$C-NMR: 222.2 (s); 130.7 (d); 125.3 (d); 55.2 (s); 39.6 (t); 35.7 (d); 33.8 (d); 29.9 (t); 28.5 (t); 23.9 (t); 18.2 (t); 17.1 (q); 12.2 (q).

R-6-Ethyl-C-10-methyl-spiro[4.5]dec-8-en-1-one (minor isomer)

Organoleptic properties: aromatic and floral odor

MS: 192 (M+, 21); 177(14); 174 (32); 163 (41); 149 (14); 145 (55); 135 (43); 125 (23); 121 (29); 119 (13); 111 (14); 108 (100); 105 (28); 93 (71); 91 (79); 81 (21); 79 (65); 77 (5/); 67 (62); 65 (30); 59 (10); 55 (45); 53 (41); 41 (86); 39 (74); 29 (54); 27 (69).

$^1$H-NMR: 5.63 (m, 1H); 5.34 (dd, J=10 Hz, 2 Hz, 1H); 2.55 (m, 1H); 2.33-2.10 (m, 3H); 1.95-1.70 (m, 5H); 1.64-1.52 (m, 1H); 1.24-1.00 (m, 2H); 0.85 (t, J=8 Hz, 3H); 0.82 (d, J=8 Hz, 3H).

$^{13}$C-NMR: 226.6 (s); 131.8 (d); 126.0 (d); 55.5 (s); 43.0 (d); 40.9 (t); 39.3 (d); 28.4 (t); 24.4 (t); 24.2 (t); 19.7 (t); 16.7 (q); 11.9 (q).

ii) R-6-ethyl-T-10-methyl-spiro[4.5]decan-1-one

R-6-Ethyl-T-10-methyl-spiro[4.5]dec-8-en-1-one (94.5%; 10 g; 0.052 mole) was dissolved in ethanol (50 g). Pd/C 5% (0.3 g) was added at RT and the mixture hydrogenated at atmospheric pressure. Filtration of the catalyst and evaporation of the solvent afforded the crude saturated ketone. Distillation under vacuum (b.p. 78° C.; 1.0 mbar) gave the pure title compound (yield=80.1%).

MS: 194 (M+, 10); 179 (6); 176 (20); 165 (58); 161 (3); 151 (8); 147 (25); 137 (22); 125 (87); 122 (53); 111 (100); 109 (57); 105 (15); 97 (15); 95 (67); 93 (20); 91 (21); 84 (16); 81 (71); 79 (33); 77 (19); 67 (54); 65 (10); 55 (36); 53 (16); 41 (29); 39 (13); 29 (7).

$^1$H-NMR: 2.36-1.64 (m, 10H); 1.55-1.38 (m, 3H); 1.06-0.76 (m, 3H); 0.91 (d, J=7 Hz, 3H); 0.87 (t, J=7 Hz, 3H).

$^{13}$C-NMR: 222.5 (s); 56.5 (s); 38.8 (t); 37.0 (d); 32.5 (d); 29.7 (t); 29.1 (t); 27.5 (t); 25.0 (t); 20.0 (t); 18.5 (t); 14.8 (q); 12.6 (q).

d) A Mixture of 7-methyl-spiro[4.5]decan-1-one and 8-methyl-spiro[4.5]decan-1-one i) A Mixture of 7-methyl-spiro[4.5]dec-7-en-1-one and 8-methyl-spiro[4.5]dec-7-en-1-one A 5000 ml stainless steel autoclave was charged with cyclopentanone (1310.4 g; 15.6 mol), isoprene (816 g; 12.0 mol), BHT (2.4 g) and 40% aqueous formaldehyde (180.6 g of pure formaldehyde; 6.02 mol). The mixture was heated to 200° C. under stirring for 7 hours. After cooling to room temperature, the reaction mixture was transferred to a separatory funnel. The aqueous phase was discarded, and the organic phase washed with brine, affording 1925 g of crude cycloadduct.

Distillation through a 15 cm Vigreux column afforded 470 g of pure cycloadduct as a mixture of isomers (ratio 35/65).

Yield: 47.6% (b.p.=107° C.; 12 mbar).

MS major isomer: 164 (M+, 65), 149 (31), 146 (50), 136 (12), 135 (12), 131 (42), 121 (25), 118 (15), 108 (32), 105 (21), 93 (100), 91 (62), 79 (68), 77 (48), 68 (30), 67 (31), 65 (21), 53 (26), 41 (37), 39 (45).

$^1$H NMR: 5.37 (m; 1H); 1.67 (s; 3H); 2.37-1.35 (m; 12H).

ii) A Mixture of 7-methyl-spiro[4.5]decan-1-one and 8-methyl-spiro[4.5]decan-1-one Were obtained from cycloadduct obtained under i) (194 g; 1.183 mol) by using the same procedure as described in Example 3.2, in 85.1% yield as a crude mixture. Distillation through a 10 cm Vigreux column afforded 167 g of 99% pure ketones as a mixture of isomers (7/41/25/27).

A distillation through a 35 cm Fischer Spaltrohr® column, afforded a fraction (21.6 g) containing isomers 8-methyl-spiro[4.5]decan-1-one (82%) and 8-methyl-spiro[4.5]decan-1-one (18%).

MS major isomer: 166 (M+, 41), 151 (4), 148 (10), 137 (8), 133 (11), 122 (12), 110 (32), 108 (15), 97 (100), 95 (86), 93 (24), 84(73), 81 (60), 70 (39), 68 (69), 55 (43), 53 (18), 41 (28), 39 (12).

$^1$H-NMR: 2.27 (m; 2H); 1.96-1.68 (m; 6H); 1.58-1.40 (m; 3H); 1.10-1.16 (m; 2H); 1.03-0.80 (m; 3H).

$^{13}$C-NMR (major isomer): 222.6 (s); 47.3 (s); 38.4 (2 t); 38.1 (2 t); 31.5 (t); 30.9 (d); 29.6 (t); 21.0 (q); 18.6 (t).

e) 10-Ethyl-8-methyl-spiro[4.5]dec-7-en-1-ol i) 10-Ethyl-8-methyl-spiro[4.5]dec-7-en-1-one A solution of propylidene cyclopentanone (124 g; 1 mol) in toluene (124 g) was cooled to 0° C. BF$_3$ etherate (10 ml) were added at 0° C. over 10 minutes. Isoprene (168 g; 2.47 mol), dissolved in toluene (168 g) was then added dropwise over 3 hours at 0° C. Stirring was continued at 0° C. for 3.5 hours. Usual work-up (see above) afforded 198 g of a crude product as a mixture of isomer (ratio 5/4/91). Distillation through a Vigreux column afforded 165 g of 96% pure cycloadduct (yield: 86%).

Organoleptic properties: fruity, eucalyptus and sage odor

MS: 192 (M+, 19), 174 (31), 163 (77), 149 (20), 145 (100), 135 (25), 121 (14), 119 (26), 107 (45), 105 (24), 96 (31), 93 (47), 91 (51), 81 (31), 79 (39) 77 (35), 67 (26), 65 (17), 55 (25), 53 (21), 43 (15), 41 (38), 39 (31), 29 (20), 27 (26).

$^1$H-NMR: 5.28 (br s; 1H); 2.40-2.31 (m; 1H); 2.18-1.70 (m; 9H); 1.66 (br s; 3H); 160-1.46 (m; 1H); 1.28-0.97 (m; 2H); 0.88 (t; J=8 Hz; 3H).

$^{13}$C-NMR: 225.2 (s); 133.9 (s); 118.2 (d); 52.2 (s); 40.1 (t); 39.2 (d); 34.8 (t); 33.2 (t); 28.3 (t); 24.3 (t); 23.3 (q); 19.0 (t); 12.0 (q).

ii) 10-Ethyl-8-methyl-spiro[4.5]dec-7-en-1-ol

10-Ethyl-8-methyl-spiro[4.5]dec-7-en-1-one (14 g; 0.073 mol) was dissolved in toluene (60 ml) and reduced using Vitride® in toluene; 40 ml) at 60-70° C. A partial conversion was observed: 22.1% ketones and 67.5% alcohols. Usual work-up (see above), followed by column chromatography on SiO$_2$ (solvent: hexane/MTBE: 9/1) afforded 95.6% pure desired product, as a mixture of isomers.

MS major isomer: 194 (M+, 3), 176 (29), 161 (10), 147 (100), 134 (12), 133 (41), 121 (17), 119 (33), 108 (17), 105 (98), 97 (20), 93 (32), 91 (32), 81 (20), 79 (22), 77 (14), 67 (17), 55 (21), 41 (21).

$^1$H-NMR: 8747: 5.25 (br s; 1H); 3.90 (m; 1H); 1.67 (br s; 3H); 1.23 (m; 1H; OH); 2.22-1.14 (m; 13H); 0.94 (t; 3H; J=7 Hz).

f) Mixture of 6,8-Dimethyl-spiro[4.5]dec-7-en-1-one and 7,9-dimethyl-spiro[4.5]dec-7-en-1-one A 5000 ml stainless steel autoclave was charged with cyclopentanone (1255 g; 14.94 mol), 2-methyl-1,3-pentadiene (1000 g; 12.2 mol), BHT (2.3 g) and 40% aq. Formaldehyde (505 g; 202 g of pure formaldehyde; 6.73 mol). The mixture was heated to 200° C. under stirring for 8 hours. After cooling to room temperature, the aqueous phase was discarded, and the organic phase washed with brine, affording a crude cycloadduct. Distillation through a 70 cm Sulzer column afforded 294 g of pure cycloadducts (b.p.=73-77° C. at 1 mbar; yield: 24.5%) as a mixture of 4 isomers in the ratio: 6/7/62/25.

MS (major isomer): 178 (M+, 38), 163 (29), 160 (33), 149 (13), 145 (35), 135 (28), 122 (13), 121 (12), 119 (11), 107 (59), 105 (17), 93 (32), 91 (40), 82 (100), 79 (32), 77 (24), 67 (56), 65 (13), 55 (15), 41 (27), 39 (19).

$^1$H-NMR (major isomers): 5.25 and 5.13 (br s, 1H); 2.44-1.80 (m, 11H); 1.67 (s, 3H); 0.89 (d, J=7 Hz, 3H); 0.81 (d, J=7 Hz, 3H).

$^{13}$C-NMR: 221.9 (s); 132.4 (s); 125.2 (d); 50.4 (s); 38.2 (t); 35.4 (d); 34.8 (t); 27.3 (t); 26.2 (t); 23.4 (q), 18.1 (t); 17.2 (q).

EXAMPLE 2

Synthesis of some Compounds According to the Invention

GC analysis were performed using an HP-INNOWax Polyethylene glycol column (30 m×0.25 mm) or an DB-1 Methyl Siloxane column (10 m×0.1 mm).

1. General Procedure for the Preparation of Mannich Bases

The ketone (1 mol), paraformaldehyde (1 mol) and dimethylamine hydrochloride (1.031 mol) were stirred in isopropanol, (50 ml). Concentrated aqueous HCl (0.6 g) was added and the reaction was heated at reflux for 30 min. After cooling to room temperature, the solid that had formed was filtered off, washed with acetone and dried. This solid was dissolved in water (200 ml) and the solution obtained was made alkaline by adding 50% aqueous NaOH and then extracted with ether. The combined organic phases were washed with brine and dried over anhydrous Na$_2$SO$_4$. Filtration and evaporation of solvents gave the final compound practically pure.

6-[(dimethylamino)methyl]-2,2-dimethylcyclohexanone

Was obtained from 2,2-dimethylcyclohexanone in 82% yield.

MS: 183 (M+, 3); 95 (9); 69 (6); 58 (100); 41 (6).

$^1$H-NMR: 1.05 (s, 3H); 1.21 (s, 3H); 1.27 (qd, J$_q$=12 Hz, J$_d$=3.7 Hz, 1H); 1.55 (td, J$_t$=12 Hz, J$_d$=3.7Hz, 1H); 1.66-1.93 (m, 4H); 2.20 (s, 6H); 2.15-2.28 (m, 1H); 2.63-2.76 (m, 2H).

2-[(dimethylamino)methyl]-4-methylcyclohexanone

Was obtained from 4-methylcyclohexanone in 57% yield and in the form of a 97:3 mixture of cis/trans isomers.

MS: 169 (M+, 2); 58 (100).

$^1$H-NMR: 1.01 (d, J=7, 3H); 1.07 (m, 1H); 1.32-1.44 (m, 2H); 1.91-2.07 (m, 1H); 2.18-2.30 (m, 2H); 2.20 (s, 6H); 2.31-2.56 (m, 3H); 2.64 (dd, $J_1$=5 Hz, $J_2$=13 Hz, 1H).

2. General Procedure for the Thermal Diels-Alder Reaction

A diene (2.53 mol), a Mannich base (0.437 mol) and hydroquinone (1.4 g) in toluene (400 ml) were heated in a steal autoclave at 170° C. (external temperature) for 23 hours. After cooling to room temperature, the reaction was washed with 5% aqueous HCl and brine. The aqueous phases were extracted with cyclohexane. The combined organic phases were dried over anhydrous $Na_2SO_4$. The residue obtained after filtration and evaporation of solvents was purified by column chromatography on silicagel (eluent: cyclohexane/ethyl acetate 19:1) and then by bulb-to-bulb distillation.

2,2-Dimethyl spiro[5.5]undec-8-en-1-one

Was obtained in 44% yield using-butadiene and 6-[(dimethylamino)methyl]-2,2-dimethyl-cyclohexanone.

B.p.=100-105° C./0.11 mbar

MS: 192 (M+, 52); 177 (6); 149 (26); 135 (13); 120 (100); 107 (26); 94 (57); 79 (91); 67 (18); 55 (21); 41 (44).

$^1$H-NMR: 1.11 (s, 3H); 1.13 (s, 3H); 1.46-1.86 (m, 7H); 1.92-2.06 (m, 4H); 2.20-2.28 (m, 1H); 5.55-5.67 (m, 2H).

Mixture of 2,2,7,9-tetramethyl spiro[5.5]undec-8-en-1-one and 2,2,8,10-tetramethyl spiro[5.5]undec-8-en-1-one Was obtained in 78% yield using 2-methyl-1,3-pentadiene and 6-[(dimethyl-amino)methyl]-2,2-dimethylcyclohexanone. GC shows a mixture of 4 isomers in the following ratio: 7/8/32/53.

B.p.=120-123° C./0.043 mbar.

MS (major isomer): 220 (M+, 55); 205 (15); 191 (6); 177 (18); 148 (12); 135 (12); 121 (44); 107 (49); 93 (33); 82 (100); 67 (32); 41 (44).

$^1$H-NMR: 0.74-0.97 (m, 3H); 1.05-1.20 (m, 7H); 1.30-2.00 (m, 11H); 2.10-2.46(m, 2H); 5.05-5.24 (m, 1H).

Mixture of 2,2,7-trimethyl spiro[5.5]undec-8-en-1-one and 2,2,10-trimethyl spiro[5.5]undec-8-en-1-one Was obtained in 21% yield using 1,3-pentadiene and 6-[(dimethylamino)methyl]-2,2-dimethylcyclohexanone. GC shows a mixture of 4 isomers in the following ratio: 5/29/32/34.

Organoleptic properties: a pleasant and natural juniper, pine, woody and balsamic odor with linalool and lavender bottom notes.

B.p.=52-63° C./0.18 mbar.

MS (major isomer): 206 (M+, 58); 191 (34); 163 (71); 147 (6); 134 (74); 121 (35); 108 (100); 93 (88); 82 (57); 67 (32); 55 (31); 41 (60).

$^1$H-NMR: 0.77-1.20 (m, 9H); 1.33-2.48 (m, 11H); 5.36-5.68 (m, 2H).

Mixture of 4,7,9-trimethyl spiro[5.5]undec-8-en-1-one and 4,8,10-trimethyl spiro[5.5]undec-8-en-1-one Was obtained in 32% yield from 2-methyl-1,3-pentadiene and 2-[(dimethylamino) methyl]-4-methylcyclohexanone. GC shows a mixture of 5 stereoisomers in the following ratio: 4.5/5.5/12/20/58.

Organoleptic properties: nice multi-odored woody, vetiveryl acetate, rosy and lilac odor.

B.p.=80° C./0.03 mbar.

MS (major isomer): 206 (M+, 53); 191 (17); 177 (18); 163 (35); 125 (18); 107 (19); 91 (22); 82 (100); 67 (28); 55 (11); 41 (13).

$^1$H-NMR: 0.74-1.20 (m, 7H); 1.23-2.73 (m, 14H); 5.13-5.28 (m, 1H).

3. General Procedure for the Reduction of Diels-Alder Adducts by a Hydride

A solution of spiro-ketone (145.6 mmol) in THF (150 ml) was added to a cold (0° C.) slurry of $LiAlH_4$ (5.7 g, 150 mmol) in THF (600 ml). The reaction was warmed up to room temperature, and then heated at 50° C. for 4 hours. After cooling to 0° C., were successively and cautiously added water (6 ml), 5% aqueous NaOH (17 ml) and again water (6 ml). The reaction was stirred at room temperature until it became a white slurry. Said slurry was dried by adding anhydrous $Na_2SO_4$. Filtration and evaporation of solvents was followed by bulb-to-bulb distillation.

(5RS,6SR,10SR)-10-ethyl-6,8-dimethyl spiro[4.5]dec-7-en-1-ol

Was obtained in 95% yield from (5RS,6SR,10SR)-10-ethyl-6,8-dimethyl spiro[4.5]dec-7-en-1-one. GC shows a 9:1 ratio of diastereoisomers.

Organoleptic properties: woody, camphoreceous, ginger odor

B.p.=100-105° C./0.36 bars.

MS: 208 (M+, 4); 190 (42); 175 (13); 161 (78); 148 (35); 133 (42); 125 (49); 119 (96); 105 (59); 91 (48); 82 (100); 67 (58); 55 (41); 41 (54).

$^1$H-NMR: 0.88-0.98 (m, 6H); 1.05-1.10 (m, 1H); 1.30-1.80 (m, 12H); 1.85-2.00 (m, 2H); 2.16-2.27 (m, 1H); 3.91-3.97 (m, 1H); 5.15-5.19 (m, 1H).

R-6-ethyl-T-10-methyl-spiro[4.5]decan-1-ol

Was obtained in 88% yield from R-6-ethyl-T-10-methyl-spiro[4.5]decan-1-one. Isomer ratio (by GC): 78/8/5.

Organoleptic properties: patchouli, borneol and camphoraceous odor

B.p.=102° C./1.7 mbar.

MS: 196 (M+, 17); 167 (18); 149 (100); 123 (63); 107 (20); 95 (60); 81 (54); 67 (47); 55 (59); 41 (68).

$^1$H-NMR: 0.80-1.10 (m, 2H); 0.89 (t, J=7.1 Hz, 3H); 0.98 (d, J=7.1 Hz, 3H); 1.29-1.84 (m, 13H); 1.97-2.05 (m, 1H); 3.87-3.94 (m, 1H).

Mixture of 6,8-dimethyl-spiro[4.5]dec-7-en-1-ol and 7,9-dimethyl-spiro[4.5]dec-7-en-1-ol Was obtained in 99% yield from a mixture of 6,8-dimethyl-spiro[4.5]dec-7-en-1-one and 7,9-dimethyl-spiro[4.5]dec-7-en-1-one. GC shows a ratio of isomers of 10/21/63.

B.p.=95° C./0.12 mbar

MS (major isomer): 180 (M$^+$, 6); 162 (77); 147 (87); 134 (86); 119 (50); 105 (98); 91 (90); 82 (100); 67 (100); 55 (48); 41 (91).

$^1$H-NMR: 0.86-1.15 (m, 3H); 1.22-2.30 (m, 15H); 3.65-3.99 (m, 1H); 5.19-5.46 (m, 1H).

4. General Procedure for the Esterification of Spiro-Alcohols

Acetyl chloride (215.4 mmol) was added slowly to a solution of alcohol (134.6 mmol), pyridine (228.8 mmol) and dimethylaminopyridine (27 mmol) in dry $CH_2Cl_2$ (600 ml). After stirring for 5 hours at room temperature, the solvent was evaporated under vacuo. The residue was taken up in pentane and the mixture washed with water, aqueous saturated $NaHCO_3$, 10% aqueous $CuSO_4$ and brine. The organic phase was dried over anhydrous $Na_2SO_4$. After filtration and evaporation of solvents, the residue was purified by bulb-to-bulb distillation.

Alternatively the esterification may be carried according to the following procedure: Acetic anhydride (12.22 mmol) was added to a solution of alcohol (6.11 mmol), pyridine (13.44 mmol) and dimethylaminopyridine (0.61 mmol) in $CH_2Cl_2$ (15 ml). The reaction was stirred for 4 hours at room temperature, then concentrated under vacuo. The residue was purified by bulb-to-bulb distillation.

R-6-ethyl-T-10-methyl-spiro[4.5]dec-1-yl acetate

Was obtained in 62% yield from R-6-ethyl-T-10-methyl-spiro[4.5]decan-1-ol.

Organoleptic properties: a very elegant woody, caryophyllene, vetiveryl acetate and slightly sandalwood odor with amber and camphoraceous undernotes.

B.p.=70° C./0.15 mbar

MS: 238 (M$^+$, 1); 209 (4); 178 (16); 163 (13); 149 (100); 135 (8); 123 (21); 107 (17); 95 (29); 81 (28); 67 (25); 43 (67); 41 (29).

$^1$H-NMR: 0.87 (d, J=6.7 Hz, 3H); 0.91 (t, J=7.3 Hz, 3H); 0.97-1.10 (m, 2H); 130-1.80 (m, 13H); 2.04 (s, 3H); 2.13-2.20 (m, 1H); 4.88 (t, J=7.3 Hz, 1H).

Mixture of 6,8-dimethyl-spiro[4.5]dec-7-en-1-yl acetate and 7,9-dimethyl-spiro[4.5]dec-7-en-1-yl acetate Was obtained in 99% yield from a mixture of 6,8-dimethyl-spiro[4.5]dec-7-en-1-ol and 7,9-dimethyl-spiro[4.5]dec-7-en-1-ol. The GC ratio of isomers was 13/8/75.

B.p.=70° C./0.06 mbar.

MS (major isomer): 222 (M$^+$, 1); 180 (5); 162 (48); 147 (53); 134 (70); 119 (37); 105 (43); 91 (37); 82 (53); 67 (43); 43 (100); 41 (36).

$^1$H-NMR: 0.82-1.20 (m, 3H); 1.32-2.27 (m, 19H).

(5RS,6SR,10SR)-10-ethyl-6,8-dimethylspiro[4.5] dec-7-en-1-yl acetate

Was obtained in 97% yield from (5RS,6SR,10SR)-10-ethyl-6,8-dimethyl spiro[4.5]dec-7-en-1-ol. GC shows a 4.5/85.1/8.4 ratio of isomers.

Organoleptic properties: a fairly strong woody, vetiveryl acetate sesquiterpenes, odor.

B.p.=78-83° C./0.078 mbar.

MS: 250 (M$^+$, 1); 190 (72); 175 (25); 161 (100); 148 (55); 134 (37); 126 (24); 119 (43); 108 (29); 93 (28); 82 (41); 67 (19); 43 (12).

$^1$H-NMR: 0.89 (d, J=7.5 Hz, 3H); 0.94 (t, J=7.3 Hz, 3H); 0.97-1.15 (m, 1H); 1.38-1.45 (m, 1H); 1.51-1.81 (m, 8H); 1.61 (broad s, 3H); 1.91-2.11 (m, 2H); 2.03 (s, 3H); 4.87 (t, J=6 Hz, 1H); 5.14-5.17 (m, 1H).

5. General Procedure for the Alkylation of Diels-Alder Adducts by MeLi

A solution of spiro-ketone (43 mmol) in dry diethylether (30 ml) was added to a solution of MeLi in dry diethylether (1.6 M, 40 ml, 64 mmol) at −78° C. The reaction was warmed up to room temperature and stirred overnight. After cooling at 0° C., water was added and the mixture was extracted with ether. The combined organic phases were washed with brine and dried over solid $Na_2SO_4$. After filtration and evaporation of solvents, the product was purified by column chromatography over silicagel (eluent=cyclohexane/ethyl acetate 29:1) and bulb-to-bulb distillation.

Mixture of 1,6,8-trimethyl-spiro[4.5]dec-7-en-1-ol and 1,7,9-trimethyl-spiro[4.5]dec-7-en-1-ol Was obtained in 40% yield from a mixture of 6,8-dimethyl-spiro[4.5]dec-7-en-1-one and 7,9-dimethyl-spiro[4.5]dec-7-en-1-one. The GC ratio of isomers was 4/4/4/5/6/74.

Organoleptic properties: borneol, camphoraceous and patchouli odor.

B.p.=68° C./0.04 mbar

MS (major isomer): 194 (M$^+$, 7); 176 (29); 161 (28); 147 (11); 136 (46); 121 (40); 119 (40); 107 (38); 105 (39); 93 (40); 91 (41); 82 (58); 67 (43); 55 (20); 43 (100).

$^1$H-NMR: 1.07 (d, J=7.1 Hz, 3H); 1.27 (s, 3H); 1.35-2.13 (m, 12H); 1.61 (s, 3H); 5.34-5.38 (m, 1H).

EXAMPLE 3

Synthesis of some Compounds According to the Invention

Ethylidene-dimethylcyclohexanone was obtained according to J. T. A. Reuvers, A. de Groot, Synthesis 1982, 1105 in the form of a mixture of E/Z isomers (87/13).

1. General Procedure for the Thermal Diels-Alder Reactions

A mixture of 5 g (32.8 mmol) ethylidene-dimethylcyclohexanone and 3 equivalents of diene was heated in an autoclave for 18 h at 200° C. After cooling and elimination of polymers by bulb to bulb distillation, the spiro-ketones were purified by flash chomatography, (pentane/ether=99/1) and bulb to bulb distillation.

2,2,11-trimethylspiro[5.5]undec-8-en-1-one

Was obtained from ethylidene-dimethylcyclohexanone and butadiene in 51% yield and in the form of a mixture of 2 isomers in the following ratio: 13/1.

Organoleptic properties: camphoraceous.

MS 206 (M+, 68); 134 (75), 93 (100), 79 (83), 41 (91).

$^1$H-NMR (main isomer): 0.73 (d: J=7, 3H), 1.08 (s, 3H), 1.10 (s, 3H), 1.50-1.85 (m, 7H), 1.97 (m, 2H), 2.22 (m, 1H), 2.33 (sept.: J=7, 1H), 5.51 (m, 1H), 5.65 (m, 1H).

2,2,9,11-tetramethylspiro[5.5]undec-8-en-1-one

Was obtained from ethylidene-dimethylcyclohexanone and isoprene in 90% yield and in the form of a mixture of 2 isomers in the following ratio: 2/3. The two isomers may be separated by preparative GC on a Supelcowax-10 column, 30 m×0.53 mm, film 2μ.

Organoleptic properties: a very natural aromatic, green and fruity odour with artemisia and ginger bottom notes.

minor isomer:

MS: 220 (M$^+$48), 192 (43), 135 (48), 122 (65), 107 (100), 93 (59), 79 (38), 67 (31), 55 (42), 41 (78).

$^1$H-NMR (C$_6$D$_6$): 0.74 (d: J=7, 3H), 1.01 (s, 3H), 1.12 (s, 3H), 1.30-1.85 (m, 8H), 1.53 (large s, 3H), 1.96 (d: J=16, 1H), 2.09 (d: J=16, 1H), 2.52 (sept.: J=7, 1H), 5.32 (m, 1H).

major isomer:

MS: 220 (M$^+$67), 148 (29), 121 (51), 107 (100), 93 (61), 82 (69), 67 (35), 55 (43), 41 (82).

$^1$H-NMR (C$_6$D$_6$): 0.75 (d: J=7, 3H), 0.99 (s, 3H), 1.12 (s, 3H), 1.25-1.75 (m, 8H), 1.56 (large s, 3H), 2.07 (m, 2H), 2.57 (sept.: J=7, 1H), 5.13 (m, 1H).

2,2,7,11-tetramethylspiro[5.5]undec-8-en-1-one

Was obtained from ethylidene-dimethylcyclohexanone and piperylene in 32% yield and in the form of a mixture of 2 isomers in the following ratio: 1/1. The two stereoisomers may be separated by preparative GC on a Supelcowax-10 column, 30 m×0.53 mm, film 2μ.

Organoleptic properties: a woody, pine and aromatic odor.

1$^{st}$ eluted peak:

MS: 220 (M+, 98); 153 (93), 107 (100), 93 (64), 68 (26), 55 (18), 41 (22).

$^1$H-NMR: 0.73 (d: J=7, 3H), 0.79 (d: J=7, 3H), 1.06 (s, 3H), 1.11 (s, 3H), 1.50-1.98 (m, 8H), 2.33 (sept.: J=7, 1H), 2.44 (m, 1H), 5.53 (m, 2H).

2$^{nd}$ eluted peak:

MS: 220 (M+, 50); 205 (100), 148 (46), 121 (35), 107 (80), 93 (42), 82 (48), 69 (16), 42 (23).

$^1$H-NMR: 0.77 (d: J=7, 3H), 0.90 (d: J=7, 3H), 1.13 (s, 6H), 1.41-1.98 (m, 8H), 2.07 (sept.: J=7, 1H), 2.73 (m, 1H), 5.29 (m, 1H), 5.60 (m, 1H).

The same reaction, performed in toluene at −20° in the presence of 1 eq. of AlCl$_3$ gave the same mixture of isomers but in a ratio of 7:1 in 75% yield after distillation.

2. General Procedure for the Hydrogenation of Spiroketones

A mixture of the spiro-ketone (0.1 mole) in 200 ml of EtOH was hydrogenated at 20° and atmospheric pressure in the presence of 100 mg of 5% Pd/C. When 1 equivalent of H$_2$ was absorbed, the mixture was filtered on Celite, concentrated under vacuum and purified by bulb to bulb distillation.

2,2,7-trimethylspiro[5.5]undecan-1-one

Was obtained from 2,2,11-trimethylspiro[5.5]undec-8-en-1-one in quantitative yield and in the form of a mixture of 2 isomers in the following ratio: 13/1.

MS (main isomer): 208 (M+, 62); 136 (42), 126 (94), 109 (56), 95 (92), 81 (92), 67 (75), 55 (71), 41 (100).

$^1$H-NMR (main isomer): 0.66 (d: J=7, 3H), 1.06 (s, 3H), 1.10 (s, 3H), 1.14-1.92, (m, 14H), 2.19 (m, 1H).

2,2,7,11-tetramethylspiro[5.5]undecan-1-one

Was obtained from 2,2,7,11-tetramethylspiro[5.5]undec-8-en-1-one in 83% yield after chromatography (pentane/ether 98/2) and in the form of a mixture of 2 isomers in the following ratio: 7/1.

MS (main isomer): 222 (M+, 30); 153 (38), 109 (100), 95 (57), 81 (39), 69 (39), 55 (43), 41 (57).

$^1$H-NMR MS (main isomer): 0.64 (d :J=7, 3H), 0.81 (d: J=7, 3H), 1.05 (s, 3H), 1.10 (s, 3H), 1.29-1.93 (m, 11H), 2.03 (s, 1H), 2.16 (s, 1H), 2.35 (s, 1H).

3. General Procedure for the Reduction of Spiroketones with LiAlH$_4$

A solution of spiro-ketone (145.6 mmol) in THF (150 ml) was added to a cold (0° C.) slurry of LiAlH$_4$ (5.7 g, 150 mmol) in THF (600 ml). The reaction was warmed up to room temperature, and then heated at 50° C. for 4 hours. After cooling to 0° C., were successively and cautiously added water (6 ml), 5% aqueous NaOH (17 ml) and again water (6 ml). The reaction was stirred at room temperature until it became a white slurry which was dried by adding anhydrous Na$_2$SO$_4$. Filtration and evaporation of solvents was followed by bulb-to-bulb distillation.

2,2,11-trimethylspiro[5.5]undec-8-en-1-ol

Was obtained from 2,2,11-trimethylspiro[5.5]undec-8-en-1-one in 94% yield and in the form of a mixture of 3 isomers in-the following ratio: 7/1/1.

MS (main isomer): 208 (M+, 22); 190 (40), 105 (80), 93 (100), 79 (38), 69 (19), 55 (21), 41 (17).

$^1$H-NMR (main isomer): 0.87 (d: J=7, 3H), 1.03 (s, 6H), 1.12-1.53 (m, 7H), 1.71 (m, 1H), 1.90 (m, 1H), 2.10 (m, 1H), 2.25 (m, 1H), 3.29 (d :J=4, 1H ; become s by addition of D$_2$O), 5.68 (m, 2H).

2,2,11-tetramethylspiro[5.5]undec-8-en-1-ol

Was obtained from 2,2,9,11-tetramethylspiro[5.5]undec-8-en-1-one in 74% yield and in the form of a mixture of 2 isomers in the following ratio: 2.3/1. The two isomers may be separated by GC on a Carbowax column, 30 m×0.25 mm, at 120°-240° C.

MS (1$^{st}$ eluted peak): 222 (M+, 12); 204 (32), 119 (72), 107 (100), 93 (31), 79 (21), 67 (28), 55 (40), 41 (59).

MS (2$^{nd}$ eluted peak): 222 (M+, 3); 204 (12), 119 (35), 107 (100), 91 (23), 79 (14), 67 (16), 55 (27), 41 (38).

$^1$H-NMR: 0.80-0.86 (m, 3H), 0.97-1.05 (m, 6H), 1.07-1.24 (m, 3H), 1.11-1.6 (m, 5H), 1.64 (s large, 3H), 1.80-2.06 (m, 2H), 2.16-2.32 (m, 1H), 6.61 (m, 1H), 3.25 (d: J=4, 1 h, become s by addition of D$_2$O), 5.38 (m, 1H).

2,2,7-trimethylspiro[5.5]undecan-1-ol

Was obtained from 2,2,7-trimethylspiro[5.5]undecan-1-one in 85% yield after chromatography (on SiO$_2$, eluent: pentane/ether=9/1) and in the form of a mixture of 2 isomers in the following ratio: 1/1 mixture. The two isomers may be separated by GC on a SPB-1 column, 30 m×0.25 mm, at 120°-240° C.

MS (1$^{st}$ eluted peak): 210 (M+, 85); 122 (52), 109 (65), 96 (78), 82 (100), 67 (40), 55 (45), 41 (29).

MS (2$^{nd}$ eluted peak): 210 (M+, 60); 122 (62), 109 (81), 96 (86), 82 (100), 67 (48), 55 (55), 41 (35).

¹H-NMR: 0.82.and 0.89 (d: J=7, 3H); 0.93, 0.98, 1.02 and 1.07 (s, 6H); 1.10-2.22 (m, 15H), 3.30 and 3.63 (d: J=6, become s by addition of D₂O, 1H).

2,2,7,11-tetramethylspiro[5.5]undecan-1-ol

Was obtained from 2,2,7,11-tetramethylspiro[5.5]undecan-1-one in quantitative yield and in the form of a mixture of 3 isomers in the following ratio: 1/16/2.

Organoleptic properties: a natural woody odor with connotation of the cedar, atlas cedar type together with terpenes bottom notes.

MS (main isomer): 224 (M+, 48); 123 (23), 109 (100), 95 (58), 82 (40), 69 (28), 55 (29), 41 (20).

¹H-NMR (main isomer): 0.83 (d: J=7, 3H), 0.97 (s, 3H), 1.06 (s, 3H), 1.22 (d: J=7, 3H), 1.10-1.93 (m, 13H), 2.17 (m, 1H), 2.35 (m, 1H), 3.37 (d: J=5, become s by addition of D₂O, 1H).

4. General Procedure for the Esterification of Alcohols

To a solution of the spiro-alcohol (1 equivalent) in pyridine (1000% in weight) was added acetic anhydride (10 equivalents) and the mixture was heated at 115° until completion of the reaction (GC). After cooling, the residue was extracted with ether, washed successively with water, 10% aqueous HCl, saturated NaHCO₃, brine, dried over Na₂SO₄ and concentrated under vacuum. The crude acetates were purified by flash chromatography (on SiO₂, eluent: pentane/ether=95/5) and by bulb to bulb distillation.

2,2,11-trimethylspiro[5.5]undec-8-en-1-yl acetate

Was obtained from 2,2,11-trimethylspiro[5.5]undec-8-en-1-ol in 58% yield and in the form of a mixture of 3 isomers in the following ratio: 7/1/1.

Organoleptic properties: an odor of the woody, amber/ambergris and cedar type.

MS (main isomer): 250 (M+, 0); 190 (99), 105 (100), 93 (66), 79 (31), 69 (16), 55 (18), 43 (37).

¹H-NMR (main isomer): 0.86 (d: J=7, 3H), 0.96 (s, 6H), 1.15-1.70 (m, 8H), 1.82 (m, 1H), 2.20 (s, 3H), 2.18 (m, 1H), 2.53 (m, 1H), 4.78 (s, 1H), 5.50 (m, 1H), 5.58 (m 1H).

2,2,9,11-tetramethylspiro[5.5]undec-8-en-1-yl acetate

Was obtained from 2,2,9,11-tetramethylspiro[5.5]undec-8-en-1-ol in quantitative yield and in the form of a mixture of 2 isomers in the following ratio: 2.3/1.

MS (minor isomer): 264 (M+, 0), 204 (47), 119 (80), 107 (79), 91 (34), 79 (21), 67 (21), 55 (35), 43 (100).

MS (major isomer): 264 (M+, 0), 204 (46), 119 (100), 107 (49), 91 (23), 79 (19), 67 (19), 55 (27), 43 (86).

¹H-NMR: 0.79-0.86 (m, 3H), 0.94 (s, 3H), 0.98 (s, 3H), 1.17-1.86 (m, 8H), 1.63 (s, large, 3H), 1.98 and 1.99 (s, 3H), 2.04-2.17 (m, 2H), 2.48 (m, 1H), 4.72 and 4.75 (s, 1H), 5.19 and 5.29 (m, 1H).

5. Procedure for the Etherification of a Spiro alcohol 7-methoxy-3,5,8,8-tetramethylspiro[5.5]undec-2-ene To a mixture of 0.36 g (2.7 mmole) of KH 30% in oil and 4 ml of dry THF at room temperature was added a solution of 0.5 g (2.25 mmole) of 2,2,9,11-tetramethylspiro[5.5]undec-8-en-1-ol in 2 ml of dry THF. After 45 minutes at 25°, 0.96 g (6.67 mmole) of CH₃I were added, the mixture was stirred for 1 hour at 25°, poured into ice, extracted with ether, washed with brine, dried on Na₂SO₄ and concentrated under vacuum. The crude product was purified by bulb to bulb distillation to give 0.55 g (99%) of pure spiro-ether and in the form of a mixture of 2 isomers in the following ratio: 2.3/1.

Organoleptic properties: a nice woody odour with vetyver, aromatic and labdanum notes.

MS (major isomer): 236 (M+, 11), 204 (46), 119 (85), 107 (100), 93 (41), 79 (26), 67 (24), 55 (38), 41 (58).

MS (minor isomer): 236 (M+, 6, 204 (30), 119 (40), 107 (100), 91 (28), 79 (18), 67 (15), 55 (26), 41 (37).

¹H-NMR: 0.78-0.85 (m, 3H), 0.98 and 0.99 (s, 6H), 1.04-2.26 (m, 13H), 2.52 (m, 1H), 2.74 (m, 1H), 3.44 and 3.46 (s, 3H), 5.26 and 5.32 (m, 1H).

EXAMPLE 4

Synthesis of some Compounds According to the Invention a) Preparation of 1,2,2-trimethylspiro[5,5]undecan-1-ol i) 1,2,2-Trimethylspiro[5,5]undec-8-en-1-ol 2,2-Dimethylspiro[5,5]undec-8-en-1-one was treated with methyllithium according to the general procedure (example 2, procedure 5) to give 1,2,2-trimethylspiro[5,5] undec-8-en-1-ol in 98% yield. The crude product was purified by bulb-to-bulb distillation (B.p.=140-150° C./0.032 mbar).

Organoleptic properties: woody, cedar odor

MS: 208 (M+, 16); 190 (41); 175 (42); 147 (86); 123 (44); 106 (100); 91 (72); 79 (74); 67 (43).

¹H-NMR: 0.97-1.17 (m, 9H); 1.20-2.35 (m, 13H); 5.50-5.70 (m, 2H).

ii) 1,2,2-Trimethylspiro[5,5]undecan-1-ol

Hydrogenation of product obtained under i) performed according to the general procedure (example 3, procedure 2) gave the title compound in 96% yield. The crude product was purified by bulb-to-bulb distillation (B.p.=80-85° C./0.064 mbar).

Organoleptic properties: a woody, and humus odor, with patchouli and amber connotation MS (major isomer): 210 (M+, 18); 192 (17); 177 (31); 149 (100); 136 (25); 126 (41);

¹H-NMR: 0.96 (s, 3H); 1.00 (s, 3H), 1.12 (s, 3H); 1.05-1.65 (m, 15H); 1.85-1.95 (m, 2H).

b) Preparation of 7-ethyl-11-methylspiro[5,5]undec-1-yl acetate

7-Ethyl-11-methylspiro[5,5]undecan-1-ol was acetylated according to the general procedure (example 2, procedure 4) to give the title compound in 91% yield, as a mixture of isomers. The crude product was purified by bulb-to-bulb distillation (B.p.=81° C./0.025 mbar).

Organoleptic properties: woody, terpenes

MS (major isomer): 252 (M+, 15); 223 (45); 192 (29); 163 (100); 123 (65); 107 (23); 95 (55); 81 (45); 67 (26).

¹H-NMR: 0.80-1.95 (m, 23H); 1.90-2.05 (m, 4H); 4.90-5.45 (m, 1H).

c) Preparation of 1-ethyl-7-methoxy-5-methylspiro[5,5]undecane i) 11-Ethyl-7-methylspiro[5,5]undec-8-en-1-ol

11-Ethyl-7-methylspiro[5,5]undec-8-en-1-one was reduced with LiAlH$_4$ according to the general procedure (example 2, procedure 3) to give the title compound in 92% yield, as a 4:1 mixture of isomers. The crude product was purified by bulb-to-bulb distillation (B.p.=102° C./0.03 mbar).

Organoleptic properties: woody

MS (major isomer): 208 (M+, 3); 190 (36); 179 (26); 161 (51); 139 (46); 121 (46); 111 (100); 105 (44); 93 (60); 81 (34); 67 (27).

¹H-NMR: 0.85-1.10 (m, 8H); 1.25-2.55 (m, 13H); 3.75 (m, 1H); 5.52 (m, 2H).

ii) 5-Ethyl-7-methoxy-1-methylspiro[5,5]undec-2-ene

11-Ethyl-7-methylspiro[5,5]undec-8-en-1-ol, obtained under i) was methylated according to the general procedure (example 3, procedure 5) to give the title compound in 95% yield, as 2.5:1 mixture of-isomers. The crude product was purified by bulb-to-bulb distillation (B.p.: 80° C./0.033 mbar).

Organoleptic properties: eucalyptus and aromatic odor

MS (major isomer): 222 (M+, 8 ); 193 (24); 190 (63); 161 (55); 153 (36); 125 (80);

¹H-NMR: 0.82-1.12 (m, 8H); 1.15-2.50 (m, 12H); 3.12-3.30 (m, 4H).

iii) 1-Ethyl-7-methoxy-5-methylspiro[5,5]undecane

5-Ethyl-7-methoxy-1-methylspiro[5,5]undec-2-ene, obtained under ii) was hydrogenated according to the general procedure (example 3, procedure 2) to give the title product in 93% yield. The crude product was purified by bulb-to-bulb distillation (E.p.=80° C./0.029 mbar).

Organoleptic properties: a pine, camphoraceous odor

MS (major isomer): 224 (M+, 55); 163 (100); 123 (57); 95 (64); 81 (43); 71 (25); 67 (23).

¹H-NMR: 0.82-1.05 (m, 8H); 1.12-1.90 (m, 16H); 3.15-3.35 (m, 4H).

d) Preparation of 1,8-dimethylspiro[4,5]decan-1-ol

A mixture of 7-methylspiro[4,5]decan-1-one and 8-methylspiro[4,5]decan-1-one and methyl lithium were reacted together according to the general procedure (example 2, procedure 5) to give the title compound in 43% yield. The crude product was purified by column chromatography on silicagel (eluent: cyclohexane/ethyl acetate 29:1) and bulb-to-bulb distillation (B.p.=68° C./0.04 mbar).

Organoleptic properties: woody, camphoraceous, cellar.

MS (major isomer): 182 (M+, 0.5); 167 (30); 164 (17); 139 (13); 135 (41); 122 (32); 108 (36); 95 (26); 93 (37); 81 (30); 79 (25); 71 (55); 43 (100).

¹H-NMR: 0.98 (d, J=7 Hz, 3H); s, 3H); 1.20-1.90 (m, 16H).

e) Preparation of 6-ethyl-1-methoxy-8-methylspiro[4,5]decane i) 10-Ethyl-1-methoxy-8-methylspiro[4,5,]dec-7-ene

10-Ethyl-8-methylspiro[4,5]dec-7-en-1-ol was O-methylated in 93% yield, using sodium hydride and methyl iodide according to the general procedure (example 3, procedure 5), to the title compound as a mixture of isomers. The crude product was purified by bulb-to-bulb distillation (B.p.=80° C./0.04 mbar).

MS (major isomer): 208 (M+, 3); 176 (47); 147 (100); 133 (30); 119 (25); 105 (90); 93 (34); 91 (41).

¹H-NMR: 0.85-0.98 (m, 3H); 1.05-2.20 (m, 16H); 3.10-3.60 (m, 4H); 5.15-5.60 (m, 1H).

ii) 6-Ethyl-1-methoxy-8-methylspiro[4,5]decane

The methyl ether prepared under A. was hydrogenated in 87% yield according to the general procedure (example 3, procedure 2) to give the title compound, as a mixture of isomers.

The product was purified by bulb-to-bulb distillation (B.p.=80° C./0.1 mbar).

Organoleptic properties: woody and cedar type

MS (major isomer): 210 (M+, 15); 149 (100); 123 (12); 107 (15); 93 (20); 81 (27).

¹H-NMR: 0.80-0.90 (m, 6H); 0.95-2.10 (m, 16H); 3.15-3.65 (m, 4H).

f) Preparation of 2,6,8/2,7,9-trimethylspiro[4,5]dec-7-en-1-ol

A mixture of 2,6,8 and 2,7,9-trimethylspiro[4,5]dec-7-en-1-one was reduced with LiAlH$_4$ according to the general procedure (example 2, procedure 3) to give the title product in 87% yield as a mixture of isomers. The crude product was purified by bulb-to-bulb distillation (B.p.=82° C./0.02 mbar).

Organoleptic properties: woody, musky, earthy odor with tonalide and cashmeran tonality as well as anisic and fruity notes MS (major isomer): 194 (M+, 2); 176 (57); 161 (69); 148 (100); 134 (21); 133 (23); 121 (73); 119 (49); 105 (54); 91 (35); 82 (39); 67 (31).

¹H-NMR: 0.85-1.20 (m, 7H); 1.25-2.20 (m, 13H); 3.28 (m, 1H); 5.05-5.55 (m, 1H).

EXAMPLE 5

Synthesis of some Compounds According to the Invention a) (1RS,6SR,11SR)-2,2,9,11-tetramethylspiro[5.5] undec-8-en-1-yl acetate and (1RS,6RS,11RS)-2,2,9, 11-tetramethylspiro[5.5]undec-8-en-1-yl acetate i) (6RS,11RS)-2,2,9,11-tetramethylspiro[5.5]undec-8-en-1-one

To a mixture of 6.7 g (0.05 mole) of AlCl$_3$ in toluene (200 ml) at 0° C. was added dropwise over 50 minutes 152.2 g (1 mole) of ethylidene-dimethylcyclohexanone. After 30 minutes at 0°, 70 g (1.1 mole) of isoprene were added dropwise over 30 minutes. After 1 h at 0°, the mixture was poured in 200 g of crushed ice and extracted twice with ether. The organic phases were washed with saturated NaHCO$_3$, twice with water and dried over Na$_2$SO$_4$, concentrated to dryness and distilled with a Vigreux apparatus to give 195 g (yield=88%) of spiroketone in the form of two main isomers (ratio 9:1).

The two isomers were separated by preparative GC on a Supelcowax-10 column, 30 m×0,53 mm, film 2μ.

(6RS,11RS)-2,2,8,11-tetramethylspiro[5.5]undec-8-en-1-one (minor isomer)

$^1$H-NMR (C$_6$D$_6$): 0.74 (d, J=7, 3H), 1.01 (s, 3H), 1.12 (s, 3H), 1.30-1.85 (m, 8H), 1.53 (large s, 3H), 1.96 (d, J=16, 1H), 2.09 (d, J=16, 1H), 2.52 (sept., J=7, 1H), 5.32 (m, 1H).
MS: 220 (M$^+$48), 192 (43), 135 (48), 122 (65), 107 (100), 93 (59), 79 (38), 67 (31), 55 (42), 41 (78).

(6RS,11RS)-2,2,9,11-tetramethylspiro[5.5]undec-8-en-5-one (major isomer)

$^1$H-NMR (C$_6$D$_6$): 0.75 (d, J=7, 3H), 0.99 (s, 3H), 1.12 (s, 3H), 1.25-1.75 (m, 8H), 1.56 (large s, 3H), 2.07 (m, 2H), 2.57 (sept., J=7, 1H), 5.13 (m, 1H).
MS: 220 (M$^+$67), 148 (29), 121 (51), 107 (100), 93 (61), 82 (69), 67 (35), 55 (43), 41 (82), ii) (1RS,6SR,11SR)-2,2,9,11-tetramethylspiro[5.5]undec-8-en-1-ol and (1RS,6RS,11RS)-2,2,9,11-tetramethylspiro[5.5]undec-8-en-1-ol By applying the general method described in Example 3, procedure 3, using (6RS,11RS)-2,2,9,11-tetramethylspiro[5.5]undec-8-en-1-one as starting compound, there were obtained two alcohols in the ratio 3 :1 which were separated by distillation with a 30 cm Fischer column.

(1RS,6SR,11SR)-2,2,9,11-tetramethylspiro[5.5]undec-8-en-1-ol (major isomer)

B.p.$_{(0.1\ mbar)}$=140°
$^1$H-NMR: 0.85 (d, J=7, 3H); 1.01 (s, 3H); 1.03 (s, 3H); 1.65 (s, 3H); 1.90 (m, 1H); 2.02 (m, 1H);2.28 (m, 1H); 2.62 (m, 1H), 3.26 (d: J=3, 1H): 5.35 (m, 1H).
MS: 222 (M+, 16); 204 (43), 134 (20), 119 (71), 107 (100), 93 (33), 82 (25), 69 (29), 55 (40), 41 (55).

(1RS,6RS,11RS)-2,2,9,11-tetramethylspiro[5.5]undec-8-en-1-ol (minor isomer)

B.p.$_{(0.7\ mbar)}$=129°
$^1$H-NMR: 0.89 (d, J=7, 3H); 0.92 (s, 3H); 0.98 (s, 3H); 1.60 (s,3H); 2.02 (m, 2H); 2.12 (m, 1H); 3.35 (d, J=5.5, 1H); 5.23 (m, 1H).
MS: 222 (M+, 2); 204 (55), 134 (30), 119 (100), 107 (63), 93 (31), 79 (21), 67 (25), 55 (37), 41 (47)

iii) (1RS,6SR,11SR)-2,2,9,11-tetramethylspiro[5.5]undec-8-en-1-yl acetate and (1RS,6RS ,11RS)-2,2,9,11-tetramethylspiro[5.5]undec-8-en-1-yl acetate By applying the general method described in Example 3, procedure 4: (1RS,6SR,11SR)-2,2,9,11-tetramethylspiro[5.5]undec-8-en-1-ol gave (1RS,6SR,11SR)-2,2,9,11-tetramethylspiro[5.5]undec-8-en-1-yl acetate in quantitative yield.

$^1$H-NMR: 0.83 (d, J=7, 3H); 0.94 (s, 3H); 0.96 (s, 3H); 1.63 (s, 3H); 1.80 (m, 1H); 1.98 (s, 3H); 2.11 (m, 2H), 2.49 (m, 1H), 4.75 (s, 11H), 5.20 (m, 1H), 5.20 (m, 1H).

MS: 264 (M+, 0); 204 (59), 134 (21), 119 (100), 107 (47), 93 (23), 79 (15), 67 (15), 55 (25), 43 (83).

(1RS,6RS,11RS)-2,2,9,11-tetramethylspiro[5.5]undec-8-en-1-ol gave (1RS,6RS,11RS)-2,2,9,11-tetramethylspiro[5.5]undec-8-en-1-yl acetate in quantitative yield.

$^1$H-NMR: 0.85 (s, 3H); 0.92 (d, J=7, 3H); 0.96 (s, 3H), 1.59 (s, 3H); 2.06 (s, 3H); 2.17 (m, 2H), 4.86 (s, 1H), 5.22 (s, 1H).
MS: 264 (M+, 0); 204 (65), 134 (32), 119 (100), 107 (62), 93 (26), 79 (16), 67 (18), 27 (55), 43 (94).

b) (1RS,6RS,11RS)-2,2,11-trimethylspiro[5.5]undec-8-en-1-ol i) (6RS,11RS)-2,2,11-trimethylspiro[5.5]undec-8-en-1-one By using the same experimental procedure as described in this example, under a.i) and using butadiene instead of isoprene the title compound, there was obtained in 83% yield with a purity >99% (no visible diastereoisomer). The physical spectra were identical to those described for 2,2,11-trimethylspiro[5.5]undec-8-en-1-one in example 3, procedure 1.

ii) (1RS,6SR,11SR)-2,2,11-trimethylspiro[5.5]undec-8-en-1-ol and (1RS,6RS,11RS)-2,2,11-trimethylspiro[5.5]undec-8-en-1-ol By applying the general method described in Example 3, procedure 3, on the ketone obtained under i) there were obtained two alcohols in the ratio 85/15 which were separated by preparative GC on a Supelcowax-10 column, 30m× 0.53 mm, film 2μ.

(1RS,6SR,11SR)-2,2,11-trimethylspiro[5.5]undec-8-en-1-ol (major isomer) spectra identical to the one described under example 3, procedure 3

(1RS,6RS,11RS)-2,2,11-trimethylspiro[5.5]undec-8-en-1-ol (minor isomer)

$^1$H-NMR: 0.89 (d, J=7, 3H), 0.93 (s, 3H), 0.99 (s, 3H), 1.74 (m, 1H), 1.90 (m, 1H), 2.03 m, 2H), 2.18 (m, 1H), 3.36 (d, J=5, 1H), 5.56 (m, 2H). MS: 208 (M+, 1); 190 (47), 147 (32), 120 (30), 105 (100), 93 (79), 79 (36), 69 (23), 55 (31), 41 (29).

c) 7-Ethyl-11-methylspiro[5,5]undecan-1-ol i) 11-Ethyl-7-methylspiro[5,5]undec-8-en-1-one (E)-propylidenecyclohexanone and isoprene reacted together in the presence of aluminum trichloride according to the general procedure given at a.i) to give the title product in 76% yield as a 4:1 mixture of isomers. The crude product was used in the next step.

Organoleptic properties: an aromatic odor
MS (major isomer): 206 (M+, 67); 191 (16); 177 (100); 149 (28); 139 (62); 125 (36); 108 (58); 93 (68); 79 (27); 67 (30).
$^1$H-NMR: 0.72-0.98 (m, 6H); 1.42-2.52 (m, 14H); 5.25-5.62 (m, 2H).

ii) 11-Ethyl-7-methylspiro[5,5]undecan-1-one

The title compound was prepared in 92% yield by hydrogenation of the cycloadduct obtained under i), according to the general procedure (example 3, procedure 2) as a 3:1 mixture of isomers. The crude product was purified by bulb-to-bulb distillation (B.p.=102° C./0.03 mbar).

MS (major isomer): 208 (M+, 47); 190 (21); 179 (82); 161 (20); 151 (31); 139 (68); 125 (100); 109 (35); 95 (74); 81 (57); 67 (41); 55 (36). $^1$H-NMR: 0.72-0.98 (m, 7H); 1.03-2.35 (m, 17H).

iii) 7-Ethyl-11-methylspiro[5,5]undecan-1-ol

LiAlH$_4$-mediated reduction of the product obtained under ii) according to the general procedure (example 2, procedure 3), gave the title compound in 88% yield, as a mixture of isomers. The crude product was purified by bulb-to-bulb distillation (B.p.=80° C./0.033 mbar).

Organoleptic properties: a woody, cedar, agarwood and patchouli odor, very natural MS (major isomer): 210 (M+, 65); 181 (37); 163 (76); 139 (20); 123 (84); 109 (23); 95 (100); 81 (68); 67 (39); 55 (45).

$^1$H-NMR: 0.72-1.00 (m, 5H); 1.05-2.35 (m, 20H); 3.70-4.20 (m, 1H).

EXAMPLE 6

Synthesis of a Mixture of 2,2,6,8 and 2,2,7,9-tetramethylspiro[4,5]dec-7-en-1-ol i) Mixture of 2,6,8 and 2,7,9-trimethylspiro[4,5]dec-7-en-1-one

N-Butyllithium (1.6 M in hexanes, 172 ml, 0.275 mol) was added to a solution of diisopropylamine (30.4 g, 0.3 mol) in THF (300 ml), while maintaining the internal temperature around −40° C. Then DMPU (1,3-dimethyl-3,4,5,6-tetrahydro-2(1H)-pyrimidone) (38.4 g, 0.3 mol) was added, followed, after 15 minutes, by a mixture of 6,8 and 7,9-dimethylspiro[4,5]dec-7-en-1-one (44.74 g, 0.25 mol) in THF (50 ml) in 30 minutes. After stirring for 30 more minutes, methyl iodide (106 g, 0.75 mol) was added rapidly. After 15 minutes, the reaction was quickly warmed up to 0° C. Acetic acid (18.6 g, 0.31 mol) was added and the reaction warmed up to room temperature. The reaction was quenched with water (500 ml) and extracted twice with pentane. Each organic fraction was treated successively with water, aqueous NaHSO$_3$, aqueous saturated NaHCO$_3$, and brine. Combined organic fractions were dried over Na$_2$SO$_4$. The liquid obtained after filtration and evaporation of solvents was purified by bulb to bulb distillation (B.p.=105° C./0.47 mbar). The title product was obtained as a colorless liquid (42.85 g, yield=89%), as a mixture of isomers.

Organoleptic properties: aromatic, camphoraceous and eucalyptus odor

MS (major isomer): 192 (M+, 59); 177 (39); 174 (24); 163 (15); 159 (36); 149 (28); 122 (29); 107 (87); 93 (34); 91 (40); 82 (100); 67 (33).

$^1$H-NMR: 0.72-1.05 (m, 3H); 1.05-1.15 (m, 3H); 1.20-2.85 (m, 13H); 5.08-5.35 (m, 1H).

ii) Mixture of 2,2,6,8 and 2,2,7,9-tetramethylspiro[4,5]dec-7-en-1-one

The title compound was prepared as a mixture of isomers from the product obtained under i) using the exact same procedure. The yield was 86%. The crude product was purified by bulb-to-bulb distillation (B.p.=88° C./0.51 mbar).

Organoleptic properties: aromatic, eucalyptus and sawdust odor

MS (major isomer): 206 (M+, 29); 191 (36); 188 (20); 173 (16); 163 (14); 122 (54); 107 (100); 93 (24); 91 (26); 82 (30); 79 (17).

$^1$H-NMR: 0.75-1.30 (m, 9H); 1.50-2.55 (m, 12H); 5.10-5.30 (m, 1H).

iii) Mixture of 2,2,6,8 and 2,2,7,9-Tetramethylspiro[4,5]dec-7-en-1-ol

LiAlH$_4$-mediated reduction of the ketone obtained under ii), using the general procedure (example 2, procedure 3), gave the title compound in 95% yield, as a mixture of isomers. The crude product was purified by bulb-to-bulb distillation (80° C./0.008 mbar).

Organoleptic properties: woody, amber odor.

MS (major isomer): 208 (M+, 2); 190 (35); 175 (51); 121 (100); 107 (20); 105 (17); 93 (16); 91 (14).

$^1$H-NMR: 0.85-1.18 (m, 9H); 1.20-2.20 (m, 13H); 3.25-3.60 (m, 1H); 5.10-5.55 (m, 1H).

EXAMPLE 7

Preparation of a Perfuming Composition

A composition of the "floral-violet" type was prepared by admixing the following ingredients:

| Ingredient | Parts by weight |
| --- | --- |
| Hexylcinnamic aldehyde | 150 |
| Cetalox ®[1] | 20 |
| 2-Pentyl-1-cyclopentol[2] | 30 |
| 10%* Farenal[3] | 50 |
| Florol ®[4] | 100 |
| Hedione ®[5] | 150 |
| Linalool | 200 |
| Mayol ®[6] | 100 |
| Myrrh essential oil | 15 |
| 10%* Rose oxide | 40 |
| Red thyme essential oil | 25 |
| Parmantheme[7] | 20 |
|  | 900 |

*in dipropyleneglycol
[1]8,12-epoxy-13,14,15,16-tetranorlabdane; origin: Firmenich SA, Geneva, Switzerland
[2]origin: Firmenich SA, Geneva, Switzerland
[3]origin: Haarmann & Reimer
[4]tetrahydro-2-isobutyl-4-methyl-4(2H)-pyranol; origin: Firmenich SA, Geneva, Switzerland
[5]methyl dihydrojasmonate; origin: Firmenich SA, Geneva, Switzerland
[6]cis-7-P-menthanol; origin: Firmenich SA, Geneva, Switzerland
[7]compounded perfumery base; origin: Firmenich SA, Geneva, Switzerland The addition of 100 parts by weight of 2,2,9,11-tetramethylspiro[5.5]undec-8-en-1-yl acetate imparted to the hereinabove-mentioned "floral-violet" composition a very nice and powerful amber/ambergris connotation and converted the starting composition into a more complex et powerful accord.

EXAMPLE 8

Preparation of a Perfuming Composition

A composition of the "woody-amber" type was prepared by admixing the following ingredients:

| Ingredient | Parts by weight |
| --- | --- |
| Benzyl acetate | 70 |
| Eugenol | 60 |
| Florol ®[1)] | 100 |
| Hedione ®[2)] | 60 |
| Iralia ® total[3)] | 180 |
| Phenethylol | 150 |
| Benzyl salicylate | 300 |
| Wardia ®[4)] | 50 |
| | 970 |

*in dipropyleneglycol
[1)]tetrahydro-2-isobutyl-4-methyl-4(2H)-pyranol; origin: Firmenich SA, Geneva, Switzerland
[2)]methyl dihydrojasmonate; origin: Firmenich SA, Geneva, Switzerland
[3)]mixture of methyl-ionone; origin: Firmenich SA, Geneva, Switzerland
[4)]compounded perfumery base; origin: Firmenich SA, Geneva, Switzerland The addition of 30 parts by weight of 2,2,9,11-tetramethylspiro[5.5]undec-8-en-1-yl acetate is sufficient to impart to the hereinabove-mentioned base composition for functional perfumery a very perceivable amber/ambergris connotation and increased the functional aspect of the above-mentioned composition.

EXAMPLE 9

Preparation of a Perfuming Composition

A masculine perfume base composition of the "woody-citrus" type was prepared by admixing the following ingredients:

| Ingredient | Parts by weight |
| --- | --- |
| Linalyl acetate | 400 |
| Bergamot essential oil | 200 |
| 8-Methoxy-2,6,6,8-tetramethyl-tricyclo[5.3.1.0(1,5)]undecane | 400 |
| Citral | 20 |
| Citronellol | 80 |
| 4-Cyclohexyl-2-methyl-2-butanol[1)] | 150 |
| Coumarin | 80 |
| Geranium essential oil | 30 |
| Hedione ® HC[2)] | 200 |
| Lavandin | 200 |
| Lyral ®[3)] | 250 |
| 50%* Oakmoss | 40 |
| Patchouli essential oil | 400 |
| Polysantol ®[4)] | 50 |
| Clary-sage essential oil | 40 |
| Vanilline | 20 |
| Vertofix coeur[3)] | 400 |
| Tamarine Base 41310[5)] | 40 |
| | 3000 |

*in dipropyleneglycol
[1)]origin: Firmenich SA, Geneva, Switzerland
[2)]methyl dihydrojasmonate; origin: Firmenich SA, Geneva, Switzerland
[3)]origin: International Flavors & Fragrances, USA
[4)]3,3-dimethyl-5-(2,2,3-trimethyl-3-cyclopenten-1-yl)-4-penten-2-ol; origin: Firmenich SA, Geneva, Switzerland
[5)]compounded perfumery base; origin: Firmenich SA, Geneva, Switzerland The addition of 300 parts by weight of 2,2,11-trimethylspiro[5.5]undec-8-en-1-ol to the hereinabove-mentioned composition boosted and exalted the patchouli note. If, instead of adding the invention compound the same amount of patchouli oil had been added to the base composition, the overall fragrance of the latter would have been less woody, rich and rooty, with a much less pronounced volume, thus having lost in performance and quality.

EXAMPLE 10

Preparation of a Perfuming Composition

A masculine perfume base composition of the "citrus-herbaceous-spicy" type was prepared by admixing the following ingredients:

| Ingredient | Parts by weight |
| --- | --- |
| Geranyl acetate | 20 |
| Linalyl acetate | 400 |
| 10%* 4-(4-Hydroxy-1-phenyl)-2-butanone | 10 |
| Bergamot essential oil | 200 |
| Cedroxide ®[1)] | 200 |
| Citral | 30 |
| Sfuma Lemon essential oil | 450 |
| 4-Cyclohexyl-2-methyl-2-butanol[2)] | 90 |
| 10%* Galbanum essential oil | 70 |
| Clove essential oil | 90 |
| Habanolide ®[3)] | 100 |
| Hedione ® HC[4)] | 30 |
| Helvetolide ®[5)] | 50 |
| Lavander essential oil | 200 |
| Lyral ®[6)] | 300 |
| Crystal moss | 20 |
| Nutmeg essential oil | 150 |
| Polysantol ®[7)] | 60 |
| Cis-3-hexenol salicylate | 30 |
| Vertofix coeur[6)] | 700 |
| Ylang Extra | 100 |
| | 3300 |

*in dipropyleneglycol
[1)]trimethyl-13-oxabicyclo-[10.1.0]-trideca-4,8-diene; origin: Firmenich SA, Geneva, Switzerland
[2)]origin: Firmenich SA, Geneva, Switzerland
[3)]pentadecenolide; origin: Firmenich SA, Geneva, Switzerland
[4)]methyl dihydrojasmonate; origin: Firmenich SA, Geneva, Switzerland
[5)](+)-(1S,1'R)-2-[1-(3',3'-dimethyl-1'-cyclohexyl)ethoxy]-2-methylpropyl propanoate; origin: Firmenich SA, Geneva, Switzerland
[6)]origin: International Flavors & Fragrances, USA
[7)]3,3-dimethyl-5-(2,2,3-trimethyl-3-cyclopenten-1-yl)-4-pentén-2-ol; origin: Firmenich SA, Geneva, Switzerland The addition of 100 parts by weight of a mixture of 2,2,7,9-tetramethylspiro[5.5]undec-8-en-1-one and its regio isomer 2,2,8,10-tetramethylspiro[5.5]undec-8-en-1-one imparted to the hereinabove-mentioned masculine composition a nice thuyonic and fruity connotation, somewhere between the Eucalyptus odor and noble laurel natural oils. However, said connotation was more substantive and long lasting, especially in the bottom notes, than similar connotations which could have been imparted by the addition of the above-mentioned naturals oils.

What is claimed is:

1. A composition comprising, as perfuming ingredient, at least one compound of formula

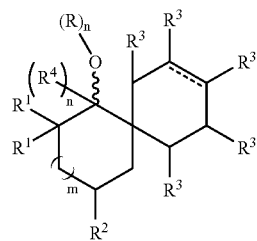
(I)

wherein the index m represents 0 or 1;
R represents a hydrogen atom, or a methyl or acetyl group;
$R^1$, $R^2$ and $R^4$ represent a hydrogen atom or a methyl group;
$R^3$ represents a hydrogen atom, or a methyl or ethyl group; two, three or four of all the $R^1$, $R^2$, $R^3$ and $R^4$ representing simultaneously a group containing at least a carbon atom; and
the wavy and dotted lines represent a double bond, in which case n represents 0;
or
the wavy line represents a single bond, in which case the index n represents 1; and the dotted line represents a single or double bond;
in the form of any one of its optical isomers or diastereomers or of a mixture thereof, and a perfume base.

2. A composition according to claim 1, wherein the perfuming ingredient is a compound of formula

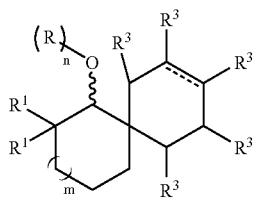
(II)

wherein n, m, R, $R^1$, $R^3$, the wavy line and the dotted line have the same meaning as indicated in claim 1.

3. A composition according to claim 1, wherein the perfuming ingredient is a compound of formula (II)

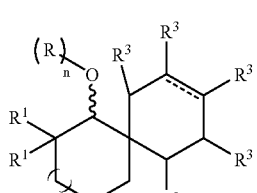
(II)

wherein the indexes m and n and the dotted and wavy lines have the same meaning as in claim 1; and
R represents a hydrogen atom or an acetyl group;
$R^1$ and $R^3$ represent a hydrogen atom or a methyl group; two, three or four of all the $R^1$ and $R^3$ representing simultaneously a methyl group and one, two or three of all the $R^3$ representing simultaneously a methyl group.

4. A composition according to claim 1, wherein the perfuming ingredient is a compound of formula

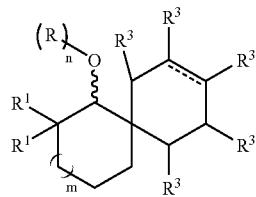
(II)

wherein the indexes m and n and the dotted and wavy lines have the same meaning as in claim 1; and
R represents a hydrogen atom or an acetyl group;
one $R^1$ is a hydrogen atom and the other $R^1$ represents a hydrogen atom or a methyl group;
$R^3$ represents a hydrogen atom or a methyl or ethyl group; two, three or four of all the $R^1$ and $R^3$ being a group containing at least a carbon atom and one, two or three of all the $R^3$, preferably non adjacent, representing a methyl or ethyl group.

5. A composition according to claim 1, wherein in that the perfuming ingredient is a compound of formula

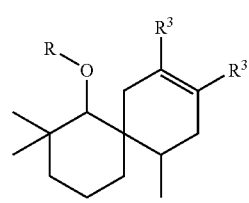
(III)

wherein R represents a hydrogen atom or an acetyl group; and
the $R^3$ are identical and represent a hydrogen atom or the $R^3$ are different and represent a hydrogen atom or a methyl group.

6. A composition according to claim 1, wherein the perfuming ingredient is a compound of formula

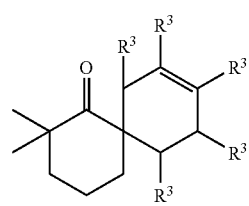
(IV)

wherein two $R^3$ represent a methyl group and the other $R^3$ represent a hydrogen atom.

7. A composition according to claim 1, wherein the perfuming ingredient is a compound of formula

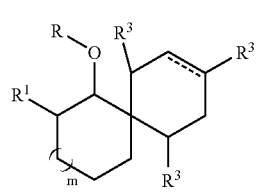
(V)

wherein R represents a hydrogen atom or an acetyl group;
$R^1$ represents a hydrogen atom or a methyl group; and
$R^3$ represents a hydrogen atom or a methyl or ethyl group and at least two $R^3$ represent a methyl group; and m is 1 and the dotted line represents a single bond, or
m is 0 and the dotted line represents a double bond.

8. A composition according to claim 1, wherein said composition comprises, as perfuming ingredient, 2,2,9,11-tetramethylspiro[5.5]undec-8-en-1-yl acetate, 2,2,11-trimethylspiro[5.5]undec-8-en-1-ol, or a mixture of 2,2,7,9-tetramethylspiro [5.5]undec-8-en-1-one and 2,2,8,10-tetramethylspiro[5.5]undec-8-en-1-one.

9. A composition according to claim 1, wherein said composition comprises, as perfuming ingredient, 2,2,11-trimethylspiro[5.5]undecan-1-ol, 2,2-dimethylspiro[5.5]undec-8-en-1-one, (1 RS,6SR,11SR)-2,2,9,11-tetramethylspiro[5.5]undec-8-en-1-yl acetate, (1RS,6RS,11RS)-2,2,11-trimethylspiro[5.5]undec-8-en-1-ol, (1RS,6RS,11RS)-2,2,9,11-tetramethyispiro[5.5]undec-8-en-1-yl acetate, 2,6,8-trimethyispiro[4.5]dec-7-en-1-ol or 7-ethyl-11-methylspiro [5.5]undecan-1-ol or a mixture of 2,2,10-trimethylspiro[5.5]undec-8-en-1-one and 2,2,7-trimethylspiro[5.5]undec-8-en-1-one or a mixture of 6,8-dimethyl-spiro[4.5]dec-7-en-1-yl acetate and 7,9-dimethyl-spiro[4.5]dec-7-en-1-yl acetate.

10. A composition consisting of at least a compound of formula (I), as defined in claim 1, and at least one perfumery carrier.

11. A perfumed article comprising:
i) at least one compound of formula (I), as defined in claim 1; and
ii) a consumer product base.

12. A perfumed article according to claim 11, wherein said consumer product base is in the form of a solid or liquid detergent, a fabric softener, a perfume, a cologne, an after-shave lotion, a perfumed soap, a shower or bath salt, mousse, oil or gel, a hygiene product, a hair care product, a shampoo, a body-care product, a deodorant, an antiperspirant, an air freshener, a cosmetic preparation, a fabric refresher, an ironing water, a paper, a wipe or a bleach.

13. A method to confer, enhance, improve or modify the odor properties of a perfuming composition or of a perfumed article, which method comprises adding to said composition or article an effective amount of a composition of claim 1 or at least a compound of formula (I) as defined in claim 1.

14. A compound of formula (I)

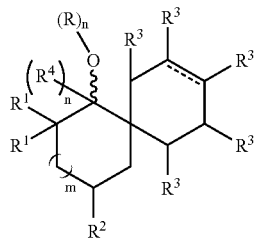

(I)

wherein the index m represents 0 or 1;
R represents a hydrogen atom, or a methyl or acetyl group;
$R^1$, $R^2$ and $R^4$ represent a hydrogen atom or a methyl group;
$R^3$ represents a hydrogen atom, or a methyl or ethyl group; two, three or four of all the $R^1$, $R^2$, $R^3$ and $R^4$ representing simultaneously a group containing at least a carbon atom; and
the wavy and dotted lines represent a double bond, in which case n represents 0;
or
the wavy line represents a single bond, in which case the index n represents 1; and the dotted line represents a single or double bond;

in the form of any one of its optical isomers or diastereomers or of a mixture thereof, provided that 2,8 dimethyl spiro[5,5]undec-8-en-1-one, 2,9-dimethyl spiro [5,5]undec-8-en-1-one, 1,9 dimethyl spiro[5,5]undec-8-en-1-ol, 1,8-dimethyl spiro[5,5]undec-8-en-1-ol, 1,7-dimethyl spiro[4,5]dec-7-en-1-ol, 1,8-dimethyl spiro[4,5]dec-7-en-1-ol, 8,9-dimethyl spiro[5,5]unddec-8-en-1-one and 7,8-dimethyl spiro[4,5]dec-7-en-1-one are excluded.

15. A compound according to claim 14, of formula

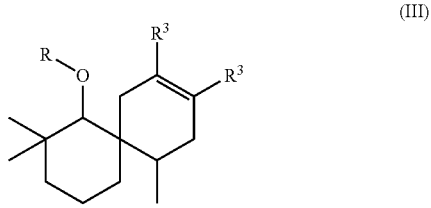

(III)

wherein R represents a hydrogen atom or an acetyl group; and
the $R^3$ are identical and represent a hydrogen atom or the $R^3$ are different and represent a hydrogen atom or a methyl group.

16. A compound according to claim 14, of formula

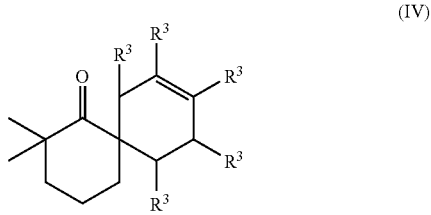

(IV)

wherein two $R^3$ represent a methyl group and the other $R^3$ represent a hydrogen atom.

17. A compound according to claim 14, of formula

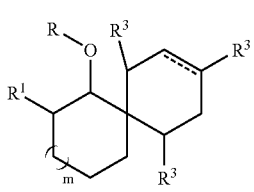

(V)

wherein R represents a hydrogen atom or an acetyl group;
$R^1$ represents a hydrogen atom or a methyl group; and
$R^3$ represents a hydrogen atom or a methyl or ethyl group and at least two $R^3$ represent a methyl group; and
m is 1 and the dotted line represents a single bond, or
m is 0 and the dotted line represents a double bond.

18. As compound according to claim 14, 2,2,9,11-tetramethylspiro[5.5]undec-8-en-1-yl acetate, 2,2,11-trimethylspiro[5.5]undec-8-en-1-ol, 2,2,11-trimethylspiro[5.5]undecan-1-ol, 2,2-dimethylspiro[5.5]undec-8-en-1-one, (1RS, 6SR,11SR)-2,2,9,11-tetramethylspiro[5.5]undec-8-en-1-yl acetate, (1RS,6RS,11RS)-2,2,11-trimethylspiro[5.5]undec-8-en-1-ol, 2,6,8-trimethylspiro[4.5]dec-7-en-1-ol, 7-ethyl-11-methylspiro[5.5]undecan-1-ol or (1RS,6RS,11RS)-2,2,9,11-tetramethylspiro[5.5]undec-8-en-1-yl acetate.

19. A compound according to claim 14, of formula (II)

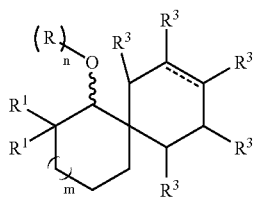
(II)

wherein:
the indexes m and n each individually represents 0 or 1;
R represents a hydrogen atom, or an acetyl group;
$R^1$ and $R^3$ represent a hydrogen atom or a methyl group;
two, three or four of all the $R^1$ and $R^3$ representing simultaneously a methyl group and one, two or three of all the $R^3$ representing simultaneously a methyl group;
$R^2$ and $R^4$ represent a hydrogen atom or a methyl group;
the wavy and dotted lines represent a double bond, in which case n represents 0; or
the wavy line represents a single bond, in which case the index n represents 1; and the dotted line represents a single or double bond.

20. A compound according to claim 14, of formula (II)

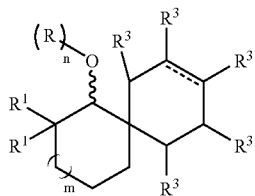
(II)

wherein:
the indexes m and n each individually represents 0 or 1;
R represents a hydrogen atom, or an acetyl group;
one $R^1$ is a hydrogen atom and the other $R^1$ represents a hydrogen atom or a methyl group;
$R^3$ represents a hydrogen atom or a methyl or ethyl group;
two, three or four of all the $R^1$ and $R^3$ being a group containing at least a carbon atom and one, two or three of all the $R^3$, preferably non adjacent, representing a methyl or ethyl group;
the wavy and dotted lines represent a double bond, in which case n represents 0; or
the wavy line represents a single bond, in which case the index n represents 1; and the dotted line represents a single or double bond.

21. A composition of at least two compounds of formula (I):

(I)

wherein the index m represents 0 or 1;
R represents a hydrogen atom, or a methyl or acetyl group;
$R^1$, $R^2$ and $R^4$ represent a hydrogen atom or a methyl group;
$R^3$ represents a hydrogen atom, or a methyl or ethyl group; two, three or four of all the $R^1$, $R^2$, $R^2$ and $R^4$ representing simultaneously a group containing at least a carbon atom; and
the wavy and dotted lines represent a double bond, in which case n represents 0;
or
the wavy line represents a single bond, in which case the index n represents 1; and the dotted line represents a single or double bond;
in the form of any one of its optical isomers or diastereomers or of a mixture thereof, provided that the compositions consisting of 2,8-dimethyl spiro[5,5]undec-8-en-1-one and 2,9-dimethyl spiro[5,5]undec-8-en-1-one, or 1,9-dimethyl spiro[5,5]undec-8-en-1-ol and 1,8-dimethyl spiro[5,5]undec-8-en-1-ol, or 1,7-dimethyl spiro[4,5]dec-7-en-1-ol and 1,8-dimethyl spiro[4,5]dec-7-en-1-ol are excluded.

22. As a composition according to claim 21, a composition containing essentially 2,2,7,9-tetramethylspiro[5.5]undec-8-en-1-one and 2,2,8,10-tetramethylspiro[5.5]undec-8-en-1-one, or a composition containing essentially 2,2,10-trimethylspiro[5.5]undec-8-en-1-one and 2,2,7-trimethylspiro[5.5]undec-8-en-1-one or a composition containing essentially 6,8-dimethyl-spiro[4.5]dec-7-en-1-yl acetate and 7,9-dimethyl-spiro[4.5]dec-7-en-1-yl acetate.

* * * * *

UNITED STATES PATENT AND TRADEMARK OFFICE
CERTIFICATE OF CORRECTION

PATENT NO. : 7,256,170 B2 Page 1 of 1
APPLICATION NO. : 10/680138
DATED : August 14, 2007
INVENTOR(S) : Vial et al.

It is certified that error appears in the above-identified patent and that said Letters Patent is hereby corrected as shown below:

Title Page:
Item (56) References Cited, OTHER PUBLICATIONS, Novikova et al. reference, after "stereochemistry, and equilibrium ratios", insert -- of --.

Column 31:
Line 25, after "the wavy and", change "doffed" to -- dotted --.

Column 33:
Line 14, change "tetramethyispiro" to -- tetramethylspiro -- .
Line 15, change "trimethyispiro" to -- trimethylspiro --.

Column 34:
Line 7, after "5]dec-7-en-l-ol, 8,9-dimethyl spiro[5,5]", change "unddec" to -- undec --.
Line 59, before "compound according to claim 14", change "As" to -- A --.

Column 36:
Line 24 (claim 21, line 7 after formula (I)), after "$R^1$, $R^2$,", change "$R^2$" to -- $R^3$ --.

Signed and Sealed this

Thirteenth Day of November, 2007

JON W. DUDAS
*Director of the United States Patent and Trademark Office*